United States Patent
Roby et al.

(10) Patent No.: US 9,918,845 B2
(45) Date of Patent: Mar. 20, 2018

(54) AUGMENT SYSTEM FOR AN IMPLANT

(71) Applicant: Zimmer, Inc., Warsaw, IN (US)

(72) Inventors: Keith A. Roby, Jersey City, NJ (US); Timothy A. Hoeman, Morris Plains, NJ (US); John Chernosky, Brick, NJ (US); Ray Zubok, Midland Park, NJ (US)

(73) Assignee: Zimmer, Inc., Warsaw, IN (US)

( * ) Notice: Subject to any disclaimer, the term of this patent is extended or adjusted under 35 U.S.C. 154(b) by 0 days.

(21) Appl. No.: 15/035,402

(22) PCT Filed: Nov. 13, 2014

(86) PCT No.: PCT/US2014/065363
§ 371 (c)(1),
(2) Date: May 9, 2016

(87) PCT Pub. No.: WO2015/073618
PCT Pub. Date: May 21, 2015

(65) Prior Publication Data
US 2016/0278925 A1    Sep. 29, 2016

Related U.S. Application Data

(60) Provisional application No. 61/903,748, filed on Nov. 13, 2013, provisional application No. 61/903,731, filed on Nov. 13, 2013.

(51) Int. Cl.
*A61F 2/38*    (2006.01)
*A61F 2/30*    (2006.01)

(52) U.S. Cl.
CPC .......... *A61F 2/389* (2013.01); *A61F 2/30734* (2013.01); *A61F 2002/30433* (2013.01);
(Continued)

(58) Field of Classification Search
CPC .................. A61F 2/3872; A61F 2/389; A61F 2002/30736; A61F 2/30734; A61B 5/4514
See application file for complete search history.

(56) References Cited

U.S. PATENT DOCUMENTS

| 4,878,791 A | 11/1989 | Kurihara et al. |
| 4,944,757 A | 7/1990 | Martinez et al. |

(Continued)

FOREIGN PATENT DOCUMENTS

| DE | 19741087 A1 | 4/1999 |
| DE | 10253888 A1 | 7/2005 |

(Continued)

OTHER PUBLICATIONS

"International Application Serial No. PCT/US2014/065362, International Search Report dated Feb. 12, 2015", 5 pgs.
(Continued)

*Primary Examiner* — Alvin Stewart
(74) *Attorney, Agent, or Firm* — Schwegman Lundberg & Woessner, P.A.

(57) ABSTRACT

Augments systems and methods for attaching two or more augments to an underside (50) of a tibial baseplate (16) are disclosed. An augment system (100) can include a first augment (102) having a superior surface (106) and an inferior surface (108), the superior surface configured for attachment to the underside of the tibial baseplate. The augment system can include a second augment (104) having a superior surface (110) and an inferior surface (112), the superior surface configured for attachment to the inferior surface of the first augment. The first and second augments can be formed of different materials. One or more additional augments can be used with the first and second augments, and the augment system can be stacked on a resected surface of the tibia. In an example, the augment that directly contacts
(Continued)

the resected surface of the tibia can be formed of a porous material, such as to facilitate bone growth.

17 Claims, 12 Drawing Sheets

(52) U.S. Cl.
 CPC ............... *A61F 2002/30434* (2013.01); *A61F 2002/30436* (2013.01); *A61F 2002/30438* (2013.01); *A61F 2002/30443* (2013.01); *A61F 2220/0041* (2013.01)

(56) References Cited

U.S. PATENT DOCUMENTS

| | | | |
|---|---|---|---|
| 4,952,106 A | 8/1990 | Kubogochi et al. | |
| 5,019,103 A | 5/1991 | Van Zile et al. | |
| 5,152,797 A | 10/1992 | Luckman et al. | |
| 5,226,917 A | 7/1993 | Schryver | |
| 5,275,603 A | 1/1994 | Ferrante et al. | |
| 5,370,693 A * | 12/1994 | Kelman | A61F 2/30724 623/16.11 |
| 5,387,241 A * | 2/1995 | Hayes | A61F 2/30734 623/20.16 |
| 5,458,637 A | 10/1995 | Hayes | |
| 5,549,689 A | 8/1996 | Epstein et al. | |
| 5,702,464 A | 12/1997 | Lackey et al. | |
| 5,984,969 A * | 11/1999 | Matthews | A61F 2/30734 623/20.11 |
| 6,005,018 A | 12/1999 | Cicierega et al. | |
| 6,074,424 A * | 6/2000 | Perrone, Jr. | A61F 2/3859 623/20.3 |
| 6,139,581 A | 10/2000 | Engh et al. | |
| 6,214,052 B1 * | 4/2001 | Burkinshaw | A61F 2/389 623/20.15 |
| 6,896,702 B2 | 5/2005 | Collazo | |
| 7,175,665 B2 | 2/2007 | German et al. | |
| 7,329,260 B2 | 2/2008 | Auger et al. | |
| 7,442,196 B2 | 10/2008 | Fisher et al. | |
| 7,578,821 B2 | 8/2009 | Fisher et al. | |
| 7,740,662 B2 | 6/2010 | Barnett et al. | |
| 7,842,093 B2 | 11/2010 | Peters et al. | |
| 7,842,094 B2 | 11/2010 | Le Bon et al. | |
| 8,016,891 B2 | 9/2011 | Ensign | |
| 8,083,746 B2 | 12/2011 | Novak | |
| 8,128,627 B2 | 3/2012 | Justin et al. | |
| 8,262,329 B2 | 9/2012 | Wille | |
| 8,443,493 B2 | 5/2013 | Seidel | |
| 8,572,818 B2 | 11/2013 | Hofmann et al. | |
| 8,932,364 B2 * | 1/2015 | Mooradian | A61F 2/30734 623/20.32 |
| 9,144,495 B2 * | 9/2015 | Lin | A61F 2/4684 |
| 9,241,801 B1 * | 1/2016 | Parry | A61F 2/30749 |
| 9,333,554 B2 | 5/2016 | Kanie et al. | |
| 9,408,699 B2 * | 8/2016 | Stalcup | A61F 2/38 |
| 2003/0074078 A1 | 4/2003 | Doubler et al. | |
| 2004/0225368 A1 * | 11/2004 | Plumet | A61F 2/3886 623/20.15 |
| 2005/0055097 A1 * | 3/2005 | Grunberg | A61B 17/8852 623/17.11 |
| 2006/0010690 A1 | 1/2006 | Bogue | |
| 2006/0015184 A1 * | 1/2006 | Winterbottom | A61F 2/44 623/18.11 |
| 2007/0088443 A1 | 4/2007 | Hanssen et al. | |
| 2008/0051908 A1 * | 2/2008 | Angibaud | A61F 2/389 623/20.32 |
| 2009/0171396 A1 | 7/2009 | Baynham et al. | |
| 2011/0009974 A1 | 1/2011 | Blaylock et al. | |
| 2011/0112651 A1 | 5/2011 | Blaylock et al. | |
| 2011/0190888 A1 * | 8/2011 | Bertele | A61F 2/446 623/17.11 |
| 2011/0190899 A1 * | 8/2011 | Pierce | A61F 2/38 623/20.32 |
| 2012/0185053 A1 | 7/2012 | Berger | |
| 2012/0209391 A1 * | 8/2012 | Cipolletti | A61F 2/389 623/18.11 |
| 2012/0310361 A1 | 12/2012 | Zubok et al. | |
| 2013/0006370 A1 * | 1/2013 | Wogoman | A61F 2/4684 623/20.16 |
| 2013/0013076 A1 * | 1/2013 | Fisher | A61F 2/4657 623/20.16 |
| 2013/0261505 A1 * | 10/2013 | Sherman | A61F 2/4657 600/595 |
| 2013/0261759 A1 * | 10/2013 | Claypool | A61F 2/4657 623/20.33 |
| 2014/0081408 A1 * | 3/2014 | Lieberman | A61F 2/3836 623/20.15 |
| 2014/0172112 A1 * | 6/2014 | Marter | A61F 2/4684 623/20.32 |
| 2014/0222155 A1 * | 8/2014 | Metzger | A61F 2/30734 623/20.15 |
| 2014/0222156 A1 * | 8/2014 | Nevins | A61F 2/3886 623/20.34 |
| 2014/0277529 A1 * | 9/2014 | Stalcup | A61F 2/38 623/20.16 |
| 2014/0277539 A1 * | 9/2014 | Cook | A61F 2/30 623/20.32 |
| 2014/0296859 A1 * | 10/2014 | Claypool | A61B 17/157 606/88 |
| 2014/0358242 A1 * | 12/2014 | Mines | A61F 2/3859 623/20.32 |
| 2015/0057758 A1 * | 2/2015 | Axelson, Jr. | A61F 2/4684 623/20.32 |
| 2015/0105782 A1 * | 4/2015 | D'Lima | A61B 17/025 606/90 |
| 2016/0324644 A1 | 11/2016 | Chernosky et al. | |

FOREIGN PATENT DOCUMENTS

| | | |
|---|---|---|
| DE | 202008011163 U1 | 1/2009 |
| EP | 2319460 A1 | 5/2011 |
| WO | WO-2013134333 A1 | 9/2013 |
| WO | WO-2015073617 A1 | 5/2015 |
| WO | WO-2015073618 A1 | 5/2015 |

OTHER PUBLICATIONS

"International Application Serial No. PCT/US2014/065362, Written Opinion dated Feb. 12, 2015", 5 pgs.

"International Application Serial No. PCT/US2014/065363, International Search Report dated Jan. 28, 2015", 6 pgs.

"International Application Serial No. PCT/US2014/065363, Written Opinion dated Jan. 28, 2015", 7 pgs.

"U.S. Appl. No. 15/035,405, Non Final Office Action dated Jul. 25, 2017", 8 pgs.

"U.S. Appl. No. 15/035,405, Preliminary Amendment Filed May 9, 2016", 8 pgs.

"European Application Serial No. 14812329.2, Response filed Feb. 20, 2017 to Communication pursuant to Rules 161(1) and 162 EPC dated Aug. 9, 2016", 17 pgs.

"European Application Serial No. 14816467.6, Response filed Feb. 20, 2017 to Communication pursuant to Rules 161(1) and 162 EPC dated Aug. 9, 2016", 16 pgs.

"International Application Serial No. PCT/US2014/065362, International Preliminary Report on Patentability dated May 26, 2016", 7 pgs.

"International Application Serial No. PCT/US2014/065363, International Preliminary Report on Patentability dated May 26, 2016", 9 pgs.

* cited by examiner

AUGMENT SYSTEM FOR AN IMPLANT

CLAIM OF PRIORITY

This application is a U.S. National Stage Application under 35 U.S.C. 371 from International Application No. PCT/US2014/065363, filed Nov. 13, 2014, and published as WO 2015/073618 A1 on May 21, 2015, which claims the benefit of U.S. Provisional Patent Application Ser. No. 61/903,748, filed on Nov. 13, 2013 and also claims the benefit of U.S. Provisional Patent Application Ser. No. 61/903,731, filed on Nov. 13, 2013, the benefit of priority of each of which is claimed hereby, and each of which are incorporated by reference herein in its entirety.

TECHNICAL FIELD

The present patent application relates to an orthopedic prosthesis, and more particularly, to an augment system and method for use with a tibial implant.

BACKGROUND

Orthopedic prostheses are commonly utilized to repair and/or replace damaged bone and tissue in the human body. For example, a knee prosthesis may be used to restore natural knee function by repairing damaged or diseased articular surfaces of the femur and/or tibia. Knee prostheses may include a femoral component implanted on the distal end of the femur, which articulates with a tibial component implanted on the proximal end of a tibia to replicate the function of a healthy natural knee. The distal portion of the femur and the proximal portion of the tibia may each by resected by an amount corresponding to a thickness of the femoral and tibial components such that the effective overall lengths of the femur and tibia remain substantially unchanged after implantation of the prosthesis.

In some cases, the proximal tibia or distal femur may have moderate to severe degeneration, trauma, or other pathology which necessitates resection of more bone than can be compensated for by traditional femoral and tibial components. In some cases, such as where a knee prosthesis is implanted in a younger patient, a revision surgery may eventually become necessary to repair or replace damaged or worn out prosthesis components. In an example, removal and replacement of the original tibial component can led to removal or damage of existing bone.

OVERVIEW

The present inventors recognize, among other things, an opportunity for an augment system for use with a knee prosthesis. The augment system can be used with a tibial baseplate and can offer versatility, flexibility, and structural support, while compensating for bone damage or other deficiencies of the tibia. The augment system described herein can be used, for example, in a joint arthroplasty procedure or in a revision procedure.

To further illustrate the augment system and methods disclosed herein, the following non-limiting examples are provided:

In Example 1, an augment system configured for attachment to a tibial baseplate can comprise a first augment having a superior surface and an inferior surface. The superior surface of the first augment can be configured for attachment to an underside of a tibial baseplate. The augment system can further comprise a second augment having a superior surface and an inferior surface. The superior surface of the second augment can be configured for attachment to the inferior surface of the first augment.

In Example 2, the augment system of Example 1 can optionally further comprise a third augment having a superior surface and an inferior surface. The superior surface of the third augment can be configured for attachment to the inferior surface of the second augment. The inferior surface of the third augment can be configured to contact a resected surface of a tibia.

In Example 3, the augment system of any one or any combination of Examples 1 or 2 can optionally be configured such that the first augment and the second augment are formed of different materials.

In Example 4, the augment system of any one or any combination of Examples 1-3 can optionally be configured such that the second augment includes a porous portion.

In Example 5, the augment system of Example 4 can optionally be configured such that the porous portion includes tantalum.

In Example 6, the augment system of any one or any combination of Examples 1-5 can optionally be configured such that the first augment is configured such that the superior surface attaches to substantially all of the underside of the tibial baseplate, and the second augment is configured such that the superior surface attaches to a portion of the inferior surface of the first augment corresponding to one of a lateral compartment or a medial compartment of the tibial baseplate.

In Example 7, the augment system of Example 6 can optionally be configured such that the second augment is a lateral augment, and the augment system further comprises a third augment configured such that a superior surface of the third augment attaches to a portion of the inferior surface of the first augment corresponding to the medial compartment of the tibial baseplate.

In Example 8, the augment system of any one or any combination of Examples 1-7 can optionally be configured such that the second augment includes one or both of a medial edge having a different height than a lateral edge in a proximal/distal direction or an anterior edge having a different height than a posterior edge in the proximal/distal direction.

In Example 9, the augment system of any one or any combination of Examples 1-8 can optionally be configured such that a thickness of the first augment is different from a thickness of the second augment.

In Example 10, the augment system of any one or any combination of Examples 1-9 can optionally further comprise a fastener configured for attaching the first and second augments to the tibial baseplate.

In Example 11, the augment system of Example 10 can optionally be configured such that the fastener can comprise a nut component, a compression component and a screw component. The nut component can have an opening formed through a top portion of the nut component and extending into a bottom portion of the nut component, and can be configured to be inserted into at least a portion of an aperture in the tibial baseplate and at least a portion of an aperture in the first augment. The compression component can be configured to be secured within an aperture in the second augment and can include an opening formed from a top end to a bottom end of the compression component and a top notch formed in the top end. The top notch can define a top diameter. The screw component can comprise a head portion having a head diameter and configured to engage with the top notch formed in the compression component, and an elongated portion configured to extend through the opening of the compression component and into the opening of the nut component. The head diameter of the head portion of the screw component can be less than the top diameter of the compression component such that the screw component can move in a radial direction relative to the compression component during insertion of the fastener to attach the first and second augments to the tibial baseplate.

In Example 12, the augment system of any one or any combination of Examples 1-11 can optionally be configured such that the superior and inferior surfaces of the second augment define a plate portion of the second augment. The second augment can further comprise a conical portion configured for insertion in a medullary canal of a tibia.

In Example 13, a tibial prosthesis configured for implantation on a tibia can comprise a tibial baseplate, a first augment and a second augment. The tibial baseplate can have a support extension extending from an underside of the tibial baseplate and configured for placement in a portion of a medullary canal of a tibia. The first augment can have a superior surface and an inferior surface and can be configured to receive the support extension of the tibial baseplate. The superior surface of the first augment can be attachable to the underside of the tibial baseplate. The second augment can have a superior surface and an inferior surface and can be configured to receive the support extension of the tibial baseplate. The superior surface of the second augment can be attachable to the inferior surface of the first augment. The first augment and the second augment can be formed of different materials.

In Example 14, the tibial prosthesis of Example 13 can optionally be configured such that the tibial baseplate, first augment and second augment each include at least one aperture. The at least one aperture of the tibial baseplate, first augment and second augment can be aligned with one another when the tibial baseplate, first augment and second augment are assembled together.

In Example 15, the tibial prosthesis of Example 14 can optionally further comprise at least one fastener for attaching the first and second augments to the tibial baseplate. The at least one fastener can comprise a nut component, a compression component, and a screw component. The nut component can have an opening formed through a top portion of the nut component and extending into a bottom portion of the nut component. The nut component can be configured to be inserted into at least a portion of an aperture in the tibial baseplate and at least a portion of an aperture in the first augment. The compression component can be configured to be secured within an aperture in the second augment and can include an opening formed from a top end to a bottom end of the compression component and a top notch formed in the top end. The top notch can define a top diameter. The screw component can comprise a head portion having a head diameter and configured to engage with the top notch formed in the compression component, and an elongated portion configured to extend through the opening of the compression component and into the opening of the nut component. The head diameter of the head portion of the screw component can be less than the top diameter of the compression component such that the screw component can move in a radial direction relative to the compression component during insertion of the at least one fastener to attach the first and second augments to the tibial baseplate.

In Example 16, a system for use in implanting a tibial prosthesis on a resected tibia can comprise a plurality of augments and a plurality of fasteners. Each augment can have at least one aperture and can be configured for attachment to at least one of a tibial baseplate or another augment such that at least two augments are attached to the tibial baseplate in a stacked relation to one another. The plurality of fasteners can have various lengths and can be configured to attach the at least two augments to the tibial baseplate.

In Example 17, the system of Example 16 can optionally be configured such that a fastener is selected from the plurality of fasteners to attach the at least two augments to the tibial baseplate based on a total thickness of the at least two augments and the tibial baseplate.

In Example 18, the system of any one or any combination of Examples 16 or 17 can optionally be configured such that the plurality of augments includes at least one augment having one or both of a medial edge having a different height than a lateral edge in a proximal/distal direction or an anterior edge having a different height than a posterior edge in the proximal/distal direction.

In Example 19, the system of any one or any combination of Examples 16-18 can optionally be configured such that the plurality of augments includes augments having different thicknesses relative to one another.

In Example 20, the system of any one or any combination of Examples 16-19 can optionally be configured such that the plurality of augments includes at least one augment sized and shaped to correspond to a periphery of the tibial baseplate.

In Example 21, the system of any one or any combination of Examples 16-20 can optionally be configured such that the plurality of augments includes at least one augment sized and shaped to correspond to one of a medial compartment or a lateral compartment of the tibial baseplate.

In Example 22, the system of any one or any combination of Examples 16-21 can optionally be configured such that the plurality of augments includes at least one augment having a porous portion.

In Example 23, the system of any one or any combination of Examples 16-22 can optionally be configured such that the plurality of augments includes at least one augment having a plate portion configured to contact a resected surface of the tibia and a medullary portion configured to extend into a canal of the tibia.

In Example 24, the system of any one or any combination of Examples 16-23 can optionally be configured such that the plurality of fasteners includes a plurality of nuts, a plurality of screws, and one or more compression bodies. The plurality of nuts and screws can have varying lengths. A diameter of a head portion of each of the screws can be less than a top diameter of each of the compression bodies such that each screw can move in a radial direction relative to the compression body during insertion of a selected nut, screw and compression body in apertures of the plurality of augments and the tibial baseplate.

In Example 25, a method of implanting a tibial prosthesis on a tibia can comprise attaching at least two augments to an underside of a tibial baseplate to create an augment system and placing the tibial baseplate and the augment system on a resected surface of the tibia. The at least two augments can be stacked relative to one another. When an orientation of the augment system on the resected surface of the tibia is not satisfactory, the method can comprise removing one or more of the at least two augments from the augment system and/or adding at least one augment to the augment system.

In Example 26, the method of Example 25 can optionally be configured such that the at least two augments include a first augment formed of a first material and a second augment formed of a second material different than the first material.

In Example 27, the method of any one or any combination of Examples 25 or 26 can optionally be configured such that the performing step is repeated until the orientation of the augment system on the resected surface of the tibia is satisfactory.

In Example 28, the method of any one or any combination of Examples 25-27 can optionally be configured such that the resected surface of the tibia is angled relative to a transverse plane, and one of the at least two augments is configured to attach to the resected surface.

In Example 29, the method of any one or any combination of Examples 25-28 can optionally be configured such that the at least two augments includes an augment having one or both of a medial edge having a different height than a lateral edge in a proximal/distal direction or an anterior edge having a different height than a posterior edge in the proximal/distal direction.

In Example 30, the method of any one or any combination of Examples 25-29 can optionally be configured such that attaching the at least two augments to the underside of the tibial baseplate includes inserting a fastener into one or more apertures in each of the at least two augments and the tibial baseplate.

In Example 31, the systems or methods of any one or any combination of Examples 1-30 can optionally be configured such that all elements or options recited are available to use or select from.

This overview is intended to provide an overview of subject matter of the present patent application. It is not intended to provide an exclusive or exhaustive explanation of the invention. The detailed description is included to provide further information about the present patent application.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

DETAILED DESCRIPTION

The present application relates to devices and methods for an augment system that can be used in or with a knee prosthesis, such as during a knee arthroplasty and/or as part of a later knee revision surgery. As described herein, an augment system can include two or more stackable augments configured to attach to a tibial baseplate and be located between the tibial baseplate and a resected surface of a tibia. The augment system can include plates of variable thickness and plates formed of different materials. The augment system can facilitate restoration of the anatomic joint line and address bone deficits on all or some of a proximal surface of a patient's tibia. In an example, the augment system can be used in combination with an implant structure configured to replace damaged bone within a medullary region of the patient's tibia.

Figure 1A:
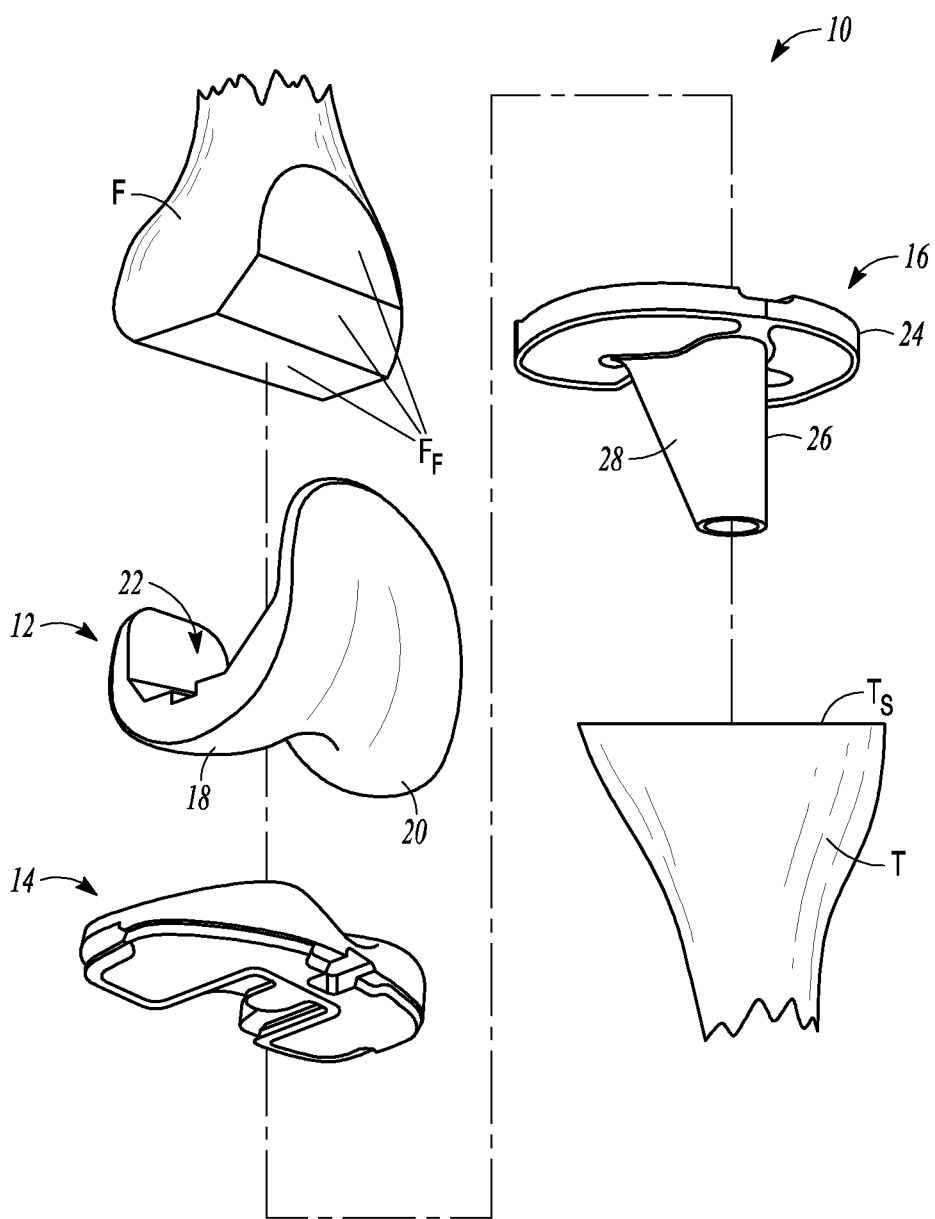
FIG. 1A is a perspective exploded view of components of a knee prosthesis, including a tibial baseplate, suitable for use in a total knee replacement surgery for a resected femur and tibia.

FIG. 1A illustrates a prosthesis system 10 for use in a total knee replacement surgical procedure. The prosthesis system 10 can include a femoral component 12, a tibial bearing component 14, and a tibial baseplate 16. The femoral component 12 can be provided for implantation upon a femur F to replace the articular surfaces of the natural femoral condyles with prosthetic condyles 18 and 20. The femur F can be prepared to receive the femoral component 12 by resection of the femoral condyles to create femoral facets $F_F$, which can be positioned and configured to abut the corresponding facets of bone-contacting surfaces 22 of the femoral component 12. The tibial baseplate 16 can be provided for implantation on a proximal resected surface $T_S$ of a tibia T. The tibial bearing component 14 can be fitted to the tibial baseplate 16 to provide a low-friction articular interface with the condyles 18 and 20 of the femoral component 12. In an example, the tibial bearing component 14 can cooperate with the tibial baseplate 16 to form a "fixed bearing" design in which the tibial bearing component 14 can be immovably affixed to the tibial baseplate 16 upon implantation. In an example, the tibial bearing component 14 can be a "mobile bearing" design in which the tibial bearing component 14 can be slidably and/or rotatably movable with respect to the tibial baseplate 16 during knee articulation.

The tibial baseplate 16 can include a plate portion 24 that can have a periphery generally shaped to correspond with the resected surface $T_S$ on the tibia T and a keel 26 configured to extend into a medullary canal of the tibia T. The keel 26 can include a pair of fins 28 extending from a distal end of the keel 26 to a distal surface of the plate portion 24.

Figure 1B:
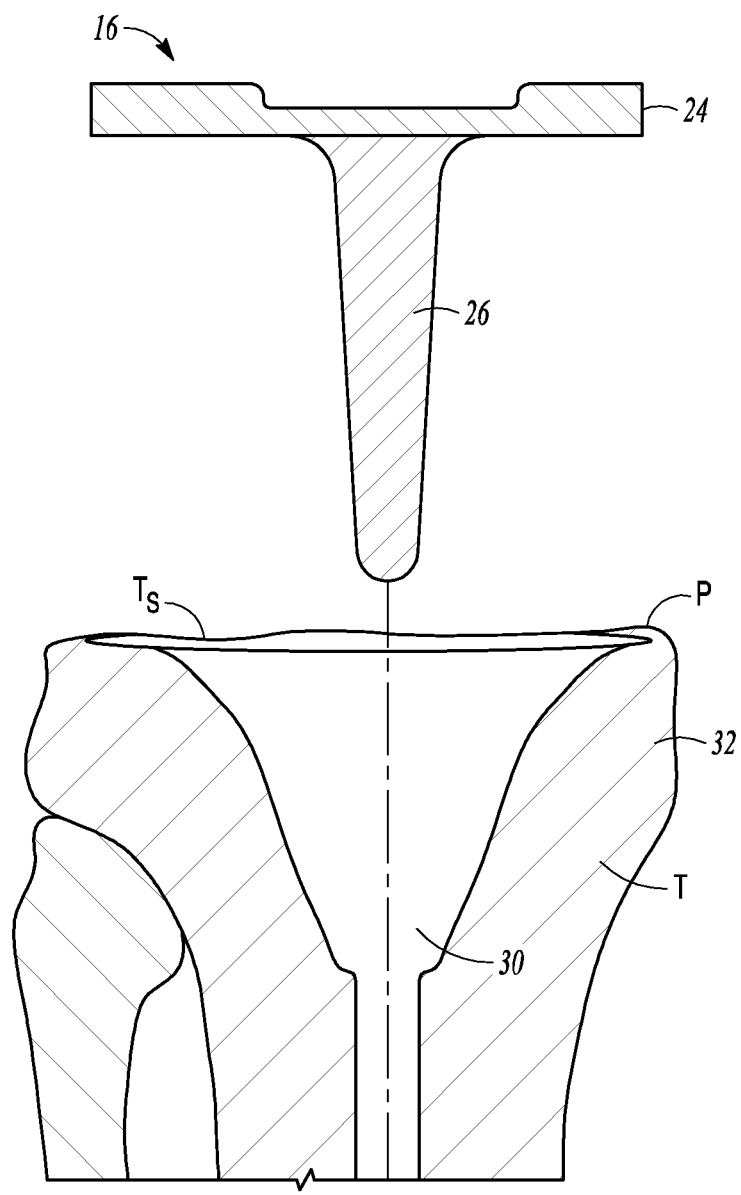
FIG. 1B is a cross-sectional view of the resected tibia and tibial baseplate of FIG. 1A.

FIG. 1B is a cross-section of the tibial baseplate 16 and the resected tibia T of FIG. 1A prior to placement of the baseplate 16 on the tibia T. As stated above, the keel 26 of the baseplate 16 can be configured to extend into an intramedullary canal 30 of the tibia T, which is surrounded by bone 32. In an example, additional bone can be removed near and around a proximal end P of the tibia T to enlarge an open area that includes the intramedullary canal 30.

As described above in reference to FIG. 1A, the tibial baseplate 16 can be used in combination with other tibial components, such as, the bearing component 14 and the femoral component 12 to form a knee prosthesis. After resecting the proximal end P of the tibia T and prior to securing the tibial baseplate 16 to the tibia T, the tibial bone near the proximal end P can commonly need to be repaired or compensated for. In a revision surgery, where one or more components of the knee prosthesis are replaced, at least some of the tibial bone can be damaged on some or all of the resected surface $T_S$ of the tibia T. In some cases, bone damage or deficiencies can be present on only one of the medial or lateral side of the tibia. Surgical variability during an original arthoplasty or revision procedure can result in the resected surface $T_S$ having a slope.

In some cases, bone cement can be used to fill in areas that originally contained natural bone or to build up a slope of the resected surface $T_S$. As an alternative or in addition to bone cement, an augment can also be used to rebuild missing bone or compensate for bone defects and variability. Although early scans can be used to generally ascertain the condition of the tibial bone, it can still be difficult to account for variability of the resected tibia T prior to surgery. An augment system, as described herein, having more than one stackable plate can provide flexibility and versatility for use with a tibial baseplate during an arthroplasty or revision procedure.

Figure 2:
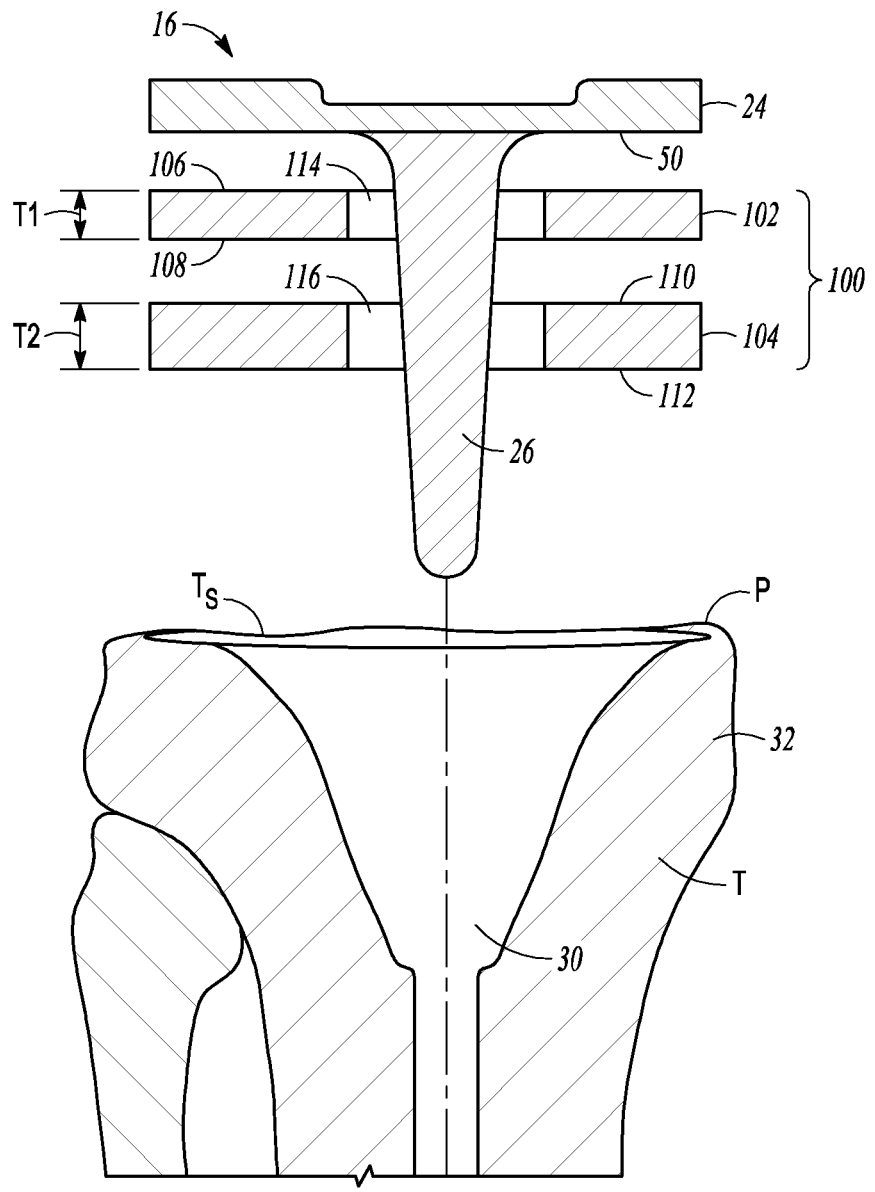
FIG. 2 is a cross-sectional view of the resected tibia and tibial baseplate of FIG. 1B in combination with an example of an augment system in accordance with the present application.

FIG. 2 is a cross-section of the tibial baseplate 16 and the resected tibia T of FIG. 1B, as well as an example of an augment system 100, which can include a first augment 102 and a second augment 104 that can be stacked relative to one another. The augment system 100 can be configured to attach to an inferior surface 50 (or underside) of the plate portion 24 of the tibial baseplate 16 and to the resected surface $T_S$ of the tibia T. Specifically, a superior surface 106 of the first augment 102 can attach to the inferior surface 50 of the plate portion 24, and an inferior surface 108 of the first augment 102 can attach to a superior surface 110 of the second augment 104. An inferior surface 112 of the second augment 104 can contact the resected surface $T_S$ on the tibia T. In an example, an initial contact between the inferior surface 112 and the resected surface $T_S$ can be a friction grip; and in some cases, depending in part on the type of material that the second augment 104 is made from, the tibial bone can grow into the second augment 104 over time. In an example, a surgeon can use bone cement or other similar attachment materials to attach the inferior surface 112 to the resected surface $T_S$.

Each of the first 102 and second 104 augments can include an opening 114 and 116, respectively, that the keel 26 of the baseplate 16 can pass through. The openings 114 and 116 can be of any size and shape suitable for receiving the keel 26 while minimizing impingement of the keel 26 with the augments 102 and 104. In other designs, the tibial baseplate 16 can have a different shaped keel (with or without fins), two or more keels, or one or more pegs in place of the keel 26. The openings 114 and 116 can be configured to accommodate various designs of the tibial baseplate 16 that can include all different types of support extensions, such as keels and pegs.

For purposes of the present application, as used herein, the term "height" can be used synonymously with "thickness" when describing a thickness dimension of the components of the augment systems described herein, as measured in a proximal/distal direction. A superior surface of a part can also be referred to herein as a proximal surface, relative to an inferior surface of the part. An inferior surface of the part can also be referred to herein as a distal surface.

The first plate 102 can have a first thickness T1 and the second plate 104 can have a second thickness T2. In an example, the first thickness T1 can be less than the second thickness T2. In other examples, the first thickness T1 and the second thickness T2 can be generally equal; and in yet other examples, the first thickness T1 can be greater than the second thickness T2. Because the second plate 104 is directly contacting the resected tibia T, it may be advantageous in some instances to have the second thickness T2 of the plate 104 be greater than the first thickness T1 of the first plate 102.

The first 102 and second 104 plates can each be made of any material, or combination of materials, suitable for implantation in a human or animal body. As described further below, the first 102 and second 104 plates can be formed of the same or of different materials.

A fastener or other types of attachment devices can be used with the augment system 100 to attach the plates 102 and 104 to the tibial baseplate 16. Holes or apertures for receiving the fasteners are not shown in the augment system 100 of FIG. 2 (or system 200 of FIG. 3), but are shown in other examples herein. An example of a fastener system usable with the augment system 100, as well as with the other examples of augment systems described herein, is described below in reference to FIGS. 8A-10. The augment system 100, as well as the other examples of augment systems described herein, can be used as a substitute for bone cement or graft material. Alternatively, the augment system 100 can be used in combination with bone cement or graft material.

Figure 3:
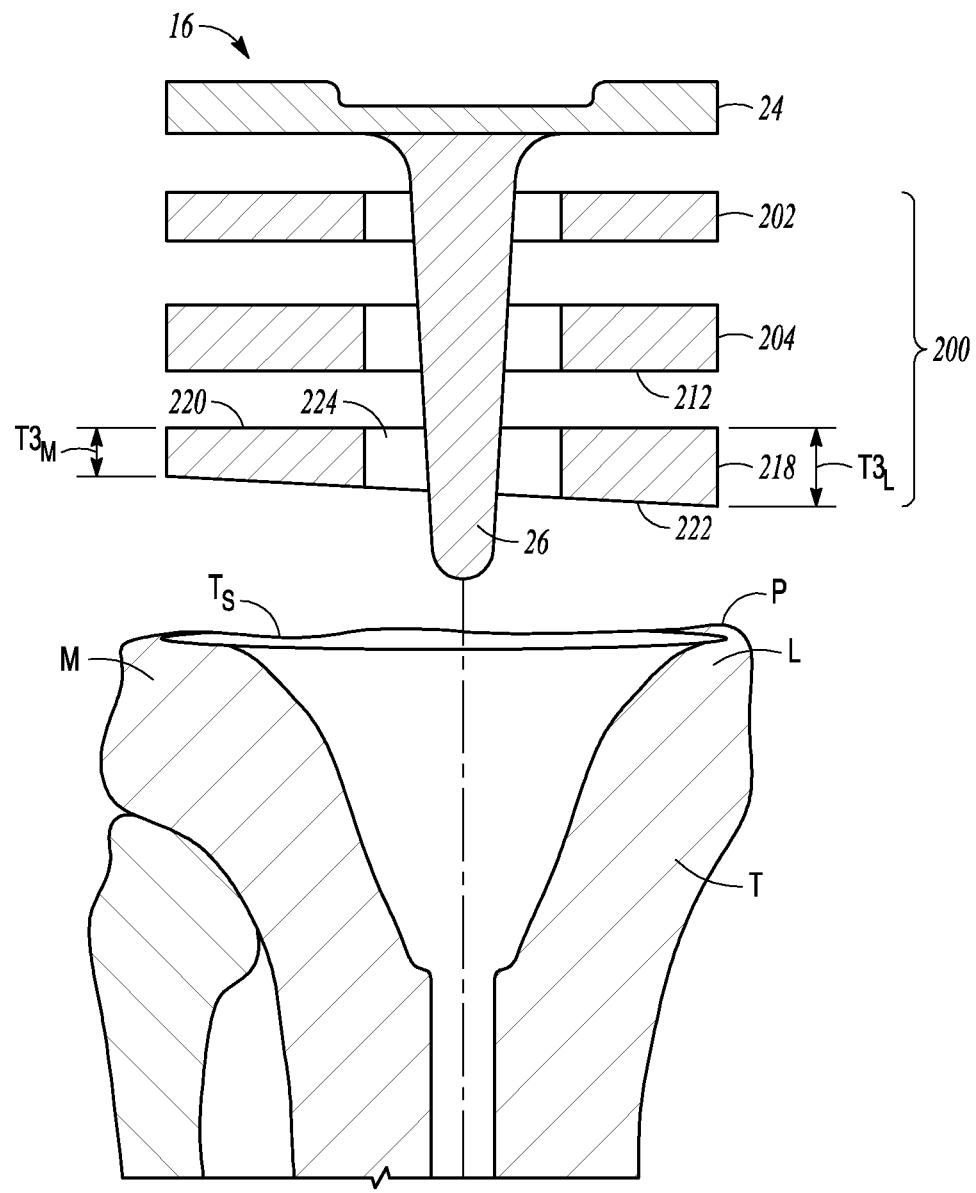
FIG. 3 is a cross-sectional view of the resected tibia and tibial baseplate of FIG. 1B in combination with an example of an augment system in accordance with the present application.

FIG. 3 is a cross-section of the tibial baseplate 16 and the resected tibia T of FIG. 1B, and an example of an augment system 200, which can include a first plate 202, a second plate 204, and a third plate 218 that can be stacked relative to one another. In an example, the first 202 and second 204 plates can be similar to the first 102 and second 104 plates of the augment system 100 of FIG. 2. The third plate 218 can include a superior surface 220 configured to attach to an inferior surface 212 of the second plate 204, and an inferior surface 222 configured to contact the resected surface $T_S$ of the tibia T. Similar to the first 202 and second 204 plates, the third plate 218 can include an aperture 224 configured for the keel 26 to extend through.

As shown in FIG. 3, the third plate 218 can have a variable thickness profile. As described further below, a medial edge of the third plate 218 can have a different height or thickness than a lateral edge of the third plate 218; additionally or alternatively, an anterior edge of the third plate 218 can have a different height or thickness than a posterior edge of the third plate 218. A variable thickness profile of the third plate 218 can be used, for example, to offset a deficiency of a knee joint (e.g., varus/valgus, anterior/posterior, or posterior/anterior sloping) present at the proximal end P of the tibia T. A variable thickness augment plate can be used to alter or compensate for an anterior/posterior slope of a tibial baseplate relative to a resected surface of the tibia. For example, in a revision procedure, the tibial baseplate 16 can be designed to be positioned at a five-degree (5°) angle on the resected tibia T, to accommodate, for example, for an anatomical tilt and to permit flexion. In such an example, the augment plate system 200 can include a variable thickness plate, like the third plate 218, to build up the resected surface $T_S$ and accommodate a slope of the inferior surface 222 relative to a transverse plane. In an example, a varying thickness augment plate can be used to address a bone deficit that can be present on only one of a medial M or a lateral side L of the tibia T or to address a bone deficit that is more prevalent on one side of the tibia T.

The third plate 218 can include a medial edge thickness $T3_M$ that is different than a lateral edge thickness $T3_L$. In the example shown in FIG. 3, the lateral edge thickness $T3_L$ can be greater than the medial edge thickness $T3_M$. In an example, the lateral edge thickness $T3_L$ can be less than the medial edge thickness $T3_M$. Due to a height or thickness difference between the medial and lateral edges, the inferior surface 222 of the third plate 218 can include a medial to lateral angle. In an example, the third plate 218 can include an anterior edge thickness that is different than a posterior edge thickness. The anterior edge thickness can be less than or greater than the posterior edge thickness. In such an example, due to a height or thickness difference between the anterior and posterior edges, the inferior surface 220 of the third plate 218 can include an anterior to posterior angle, relative to a transverse plane. The wedge-like shape of the third plate 218, in a medial-lateral and/or a posterior-anterior direction can be used, as described above, to compensate for a bone deficiency on the resected surface $T_S$ or for a slope of the resected surface $T_S$ relative to the tibial baseplate 16.

The augment system 100 of FIG. 2 includes two stacked plates, both of generally uniform thickness, and the augment system 200 of FIG. 3 includes three stacked plates, with one plate of variable thickness. It is recognized that the augment system described herein can include any number of plates, each having a generally uniform or variable thickness, and any combination of thicknesses from plate to plate. An overall thickness or a total spacing of the augment system between the inferior surface of the tibial baseplate and the resected surface of the tibia T can be any amount, based on a unique shape and condition of a particular patient's tibia. As described below in reference to FIGS. 4-7B, alternative designs of the augment system can be used, for example, having separate medial and lateral augments as an alternative to the variable thickness plate 218 of the augment system 200. Moreover, as further described below, any type or material or any combination of materials can be used for the various augment plates.

One or more of the plates 202, 204 and 218 can be formed of the same material(s) or each of the plates 202, 204 and 218 can be formed of different materials. The plates 202, 204 and 218 can each be made of any material, or combination of materials, suitable for implantation in a human or animal body. This description regarding the materials used to form the plates 202, 204 and 218 is also applicable to any of the other examples of augment systems shown and described herein. Because the design of the augment systems described herein includes multiple stackable plates, multiple materials can be used and the material of a particular plate can be selected based on that particular plate's position within the augment system, a particular bone defect, or a particular need of the patient.

Any combination of materials can be used to form the augment plates described herein. In an example, the first 202, second 204, and third 218 plates can be formed of a metal or metal alloy, such as for example, titanium or cobalt-chrome alloys. In another example, one or both of the first 202 and second 204 plates can be formed of a polymer, such as polyethylene, or a ceramic material. In an example, the third plate 218 can be formed of a porous metal to facilitate ingrowth of bone over time, as further described below. Other materials or combinations can include, but are not limited to, tantalum, a base material coated with another material, composites of two or more materials, such as, for example, a porous metal (such as tantalum) and a solid metal (such as titanium), or a polyethylene material molded into porous metal. Referring back to the augment system 100 of FIG. 2, because the augment system 100 includes two plates as shown, the second plate 104 is configured as the plate that has a bone contacting surface, and as such, the second plate 104 can be formed of a porous metal similar to the third plate 218 of the augment system 200. The description herein of a plate formed of a porous structure can apply to any of the plates configured for use in the augment systems described herein, particularly, for example, those plates that have an inferior surface that is configured as a bone contacting surface. In some examples, it may be desirable to avoid having an inner plate (i.e. a plate that does not include a bone contacting surface) formed of a porous metal in order to avoid potential soft tissue impingement.

In an example, the third plate 218 or the second plate 104, or any of the other augment plates described and shown herein, can be formed of a porous structure, such as to facilitate bone ingrowth or regrowth. A highly porous metal structure can incorporate one or more of a variety of biocompatible metals. Such structures are particularly suited for contacting bone and soft tissue, and in this regard, can be useful as a bone substitute and as cell and tissue receptive material, for example, by allowing tissue to grow into the porous structure over time to enhance fixation (i.e., osseointegration) between the structure and surrounding bodily structures. According to certain embodiments of the present disclosure, an open porous metal structure may have a porosity as low as 55%, 65%, or 75% or as high as 80%, 85%, or 90%, or within any range defined between any pair of the foregoing values. An example of an open porous metal structure is produced using Trabecular Metal™ Technology available from Zimmer, Inc., of Warsaw, Ind. Trabecular Metal™ is a trademark of Zimmer, Inc. Such a material may be formed from a reticulated vitreous carbon foam substrate which is infiltrated and coated with a biocompatible metal, such as tantalum, by a chemical vapor deposition ("CVD") process in the manner disclosed in detail in U.S. Pat. No. 5,282,861 and in Levine, B. R., et al., "Experimental and Clinical Performance of Porous Tantalum in Orthopedic Surgery", Biomaterials 27 (2006) 4671-4681, the disclosures of which are expressly incorporated herein by reference. In addition to tantalum, other biocompatible metals may also be used in the formation of a highly porous metal structure such as titanium, a titanium alloy, cobalt chromium, cobalt chromium molybdenum, tantalum, a tantalum alloy, niobium, or alloys of tantalum and niobium with one another or with other metals. It is also within the scope of the present disclosure for a porous metal structure to be in the form of a fiber metal pad or a sintered metal layer, such as a Cancellous-Structured Titanium™ (CSTi™) layer. CSTi™ porous layers are manufactured by Zimmer, Inc., of Warsaw, Ind. Cancellous-Structured Titanium™ and CSTi™ are trademarks of Zimmer, Inc.

Generally, a highly porous metal structure will include a large plurality of metallic ligaments defining open voids (i.e., pores) or channels therebetween. The open spaces between the ligaments form a matrix of continuous channels having few or no dead ends, such that growth of soft tissue and/or bone through open porous metal is substantially uninhibited. Thus, the open porous metal may provide a lightweight, strong porous structure which is substantially uniform and consistent in composition, and provides a matrix (e.g., closely resembling the structure of natural cancellous bone) into which soft tissue and bone may grow to provide fixation of the implant to surrounding bodily structures. According to some aspects of the present disclosure, exterior surfaces of an open porous metal structure can feature terminating ends of the above-described ligaments. Such terminating ends can be referred to as struts, and they can generate a high coefficient of friction along an exposed porous metal surface. Such features can impart an enhanced affixation ability to an exposed porous metal surface for adhering to bone and soft tissue. Also, when such highly porous metal structures are coupled to an underlying substrate, a small percentage of the substrate may be in direct contact with the ligaments of the highly porous structure, for example, approximately 15%, 20%, or 25%, of the surface area of the substrate may be in direct contact with the ligaments of the highly porous structure.

An open porous metal structure may also be fabricated such that it comprises a variety of densities in order to selectively tailor the structure for particular orthopedic applications. In particular, as discussed in the above-incorporated U.S. Pat. No. 5,282,861, an open porous metal structure may be fabricated to virtually any desired density, porosity, and pore size (e.g., pore diameter), and can thus be matched with the surrounding natural tissue in order to provide an improved matrix for tissue ingrowth and mineralization. According to certain embodiments, an open porous metal structure may be fabricated to have a substantially uniform porosity, density, and/or void (pore) size throughout, or to comprise at least one of pore size, porosity, and/or density being varied within the structure. For example, an open porous metal structure may have a different pore size and/or porosity at different regions, layers, and surfaces of the structure. The ability to selectively tailor the structural properties of the open porous metal, for example, enables tailoring of the structure for distributing stress loads throughout the surrounding tissue and promoting specific tissue ingrown within the open porous metal.

In other embodiments, an open porous metal structure may comprise an open cell polyurethane foam substrate coated with Ti-6Al-4V alloy using a low temperature arc vapor deposition process. Ti-6Al-4V beads may then be sintered to the surface of the Ti-6Al-4V-coated polyurethane foam substrate. Additionally, another embodiment of an open porous metal structure may comprise a metal substrate combined with a Ti-6Al-4V powder and a ceramic material, which is sintered under heat and pressure. The ceramic particles may thereafter be removed leaving voids, or pores, in the substrate. An open porous metal structure may also comprise a Ti-6Al-4V powder which has been suspended in a liquid and infiltrated and coated on the surface of a polyurethane substrate. The Ti-6Al-4V coating may then be sintered to form a porous metal structure mimicking the polyurethane foam substrate. Further, another embodiment of an open porous metal structure may comprise a porous metal substrate having particles, comprising altered geometries, which are sintered to a plurality of outer layers of the metal substrate. Additionally, an open porous metal structure may be fabricated according to electron beam melting (EBM) and/or laser engineered net shaping (LENS). For example, with EBM, metallic layers (comprising one or more of the biomaterials, alloys, and substrates disclosed herein) may be coated (layer by layer) on an open cell substrate using an electron beam in a vacuum. Similarly, with LENS, metallic powder (such as a titanium powder, for example) may be deposited and coated on an open cell substrate by creating a molten pool (from a metallic powder) using a focused, high-powered laser beam.

Because the plate 218, having the inferior or bone contacting surface 222, for example, can be formed of a porous material, like the above-described porous tantalum, the plate 218 can promote bone ingrowth and promote secure and stable fixation of the augment system 200 to the tibia T. The porous tantalum material can also be used in other examples of augment systems. By being able to achieve a strong fixation to the bone, the augment systems described herein can be used without requiring bone cement for fixation of the augment system to the bone, although it is recognized that bone cement can still be used. A lack of bone cement can facilitate bone ingrowth by allowing bone to interdigitate with a bone contacting surface of the augment system 200. This can provide stronger and more secure fixation than can sometimes be achieved between solid metal, or other similar materials, and bone, using bone cement. As such, in some instances, all or a portion of the augment system 200 can remain in the body during a revision surgery and provide a strong, stable and reusable structure for a new tibial baseplate and/or other knee prosthesis components.

Figure 4:
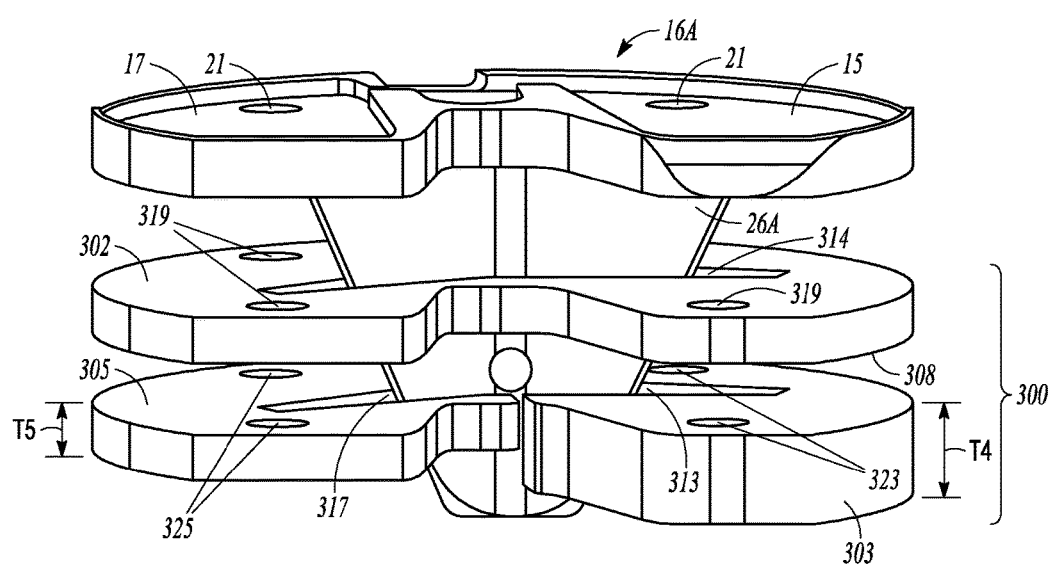
FIG. 4 is a front exploded view of an example of a tibial baseplate and augment system in accordance with the present application.

FIG. 4 shows a tibial baseplate 16A, that can be similar to the tibial baseplate 16 of FIGS. 1A-3, and an example of an augment system 300, which can include a first plate 302, a medial plate 303 and a lateral plate 305. The first plate 302 and the medial plate 303 can be in stacked relation, and the first plate 302 and the lateral plate 305 can be in stacked relation. (FIG. 4 shows a posterior end of the tibial baseplate 16A, whereas FIGS. 1A-3 show an anterior end of the tibial baseplate 16.) The first plate 302 can be similar to the first plates 102 and 202 of systems 100 and 200, respectively. A thickness of the first plate 302 can be generally uniform and can be equal to, more than or less than a thickness of the first plates 102 or 202.

The medial plate 303 can be configured in size and shape to generally correspond to a medial compartment 15 of the tibial baseplate 16A and the lateral plate 305 can be configured in size and shape to generally correspond to a lateral compartment 17 of the tibial baseplate 16A. As such, the medial plate 303 can be configured to contact an inferior surface 308 of the first plate 302 on a medial side corresponding to the medial compartment 15 of the tibial baseplate 16A, and the lateral plate 305 can be configured to contact the inferior surface 308 of the first plate 302 on a lateral side corresponding to the lateral compartment 17 of the tibial baseplate 16A. In an example, the tibial baseplate 16A can be side specific, and the tibial baseplate 16A of FIG. 4 can be a left tibial plate configured for placement on a resected tibia for a left leg. In other examples, the augment system 300, as well as the other augment systems described herein, can be used with tibial baseplates that are not side specific to a right or a left leg. The tibial baseplates can be symmetric or asymmetric in design.

As shown in FIG. 4, in an example, the medial plate 303 can have a thickness T4 that is greater than a thickness T5 of the lateral plate 305. In another example, the thickness T4 can be less than the thickness T5. As similarly described above in reference to the third plate 218 of FIG. 3, by having differing thicknesses relative to one another, the medial 303 and lateral 305 plates can be used to compensate for deficiencies or abnormalities of a tibia or for variability in the surgical procedure for resecting the tibia. In another example, the thicknesses T4 and T5 can be generally equal.

In an example, one or both of the medial plate 303 and the lateral plate 305 can each have a generally uniform thickness such that a medial edge of the medial plate 303 can be generally equal to a lateral edge of the medial plate 303, and a medial edge of the lateral plate 305 can be generally equal to a lateral edge of the lateral plate 305. In another example, one or both of the medial plate 303 and the lateral plate 305 can have a variable thickness, as similarly described above in reference to the plate 218 of the augment system 200 of FIG. 3.

Similar to the openings 114 and 116 of the first 102 and second 104 plates, each of the first plate 302, medial plate 303 and lateral plate 305 can include an opening 314, 313, and 317, respectively, which is configured to receive the keel 26A.

As shown in FIG. 4, each of the components of the augment system 300 can include one or more holes for receiving a fastener configured to assemble the augment system 300 to the tibial baseplate 16A. In an example, the first plate 302 can include four apertures 319 (only three of the four apertures are visible in FIG. 4), which can correspond to four apertures 21 on the tibial baseplate 16A (only two of which are visible in FIG. 4). In an example, the medial plate 303 can include two apertures 323 that can correspond to two of apertures 21 and 319, and the lateral plate 305 can include two apertures 325 that can correspond to two of apertures 21 and 319. The augment system 300 can include more or less apertures, each for receiving a fastener, than what is shown in FIG. 4.

As described below, any type of fastener can be used to attach the augment system 300 to the tibial baseplate 16A. This also applies to the other augment systems described herein. In an example, one or more of the fasteners can extend from the bottom of the augment system 300 to the top of the tibial baseplate 16A. In an example, one or more of the fasteners can extend from the top of the tibial baseplate 16A to the bottom of the augment system 300. Examples of fasteners usable with the augment systems described herein are shown in FIGS. 6 and 8A-10.

Figure 5:
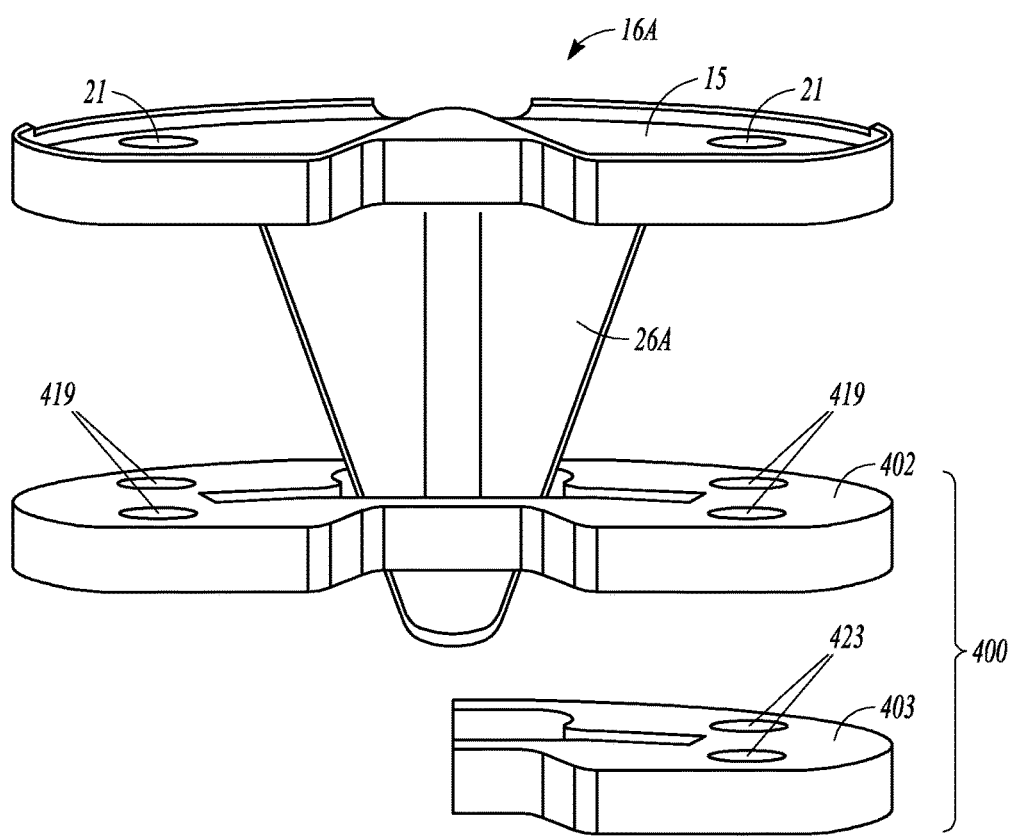
FIG. 5 is a front exploded view of an example of a tibial baseplate and augment system in accordance with the present application.

FIG. 5 shows the tibial baseplate 16A of FIG. 4, and an example of an augment system 400, which can include a first plate 402 and a medial plate 403. As shown in FIG. 5, in an example, the augment system 400 can exclude a lateral plate like the lateral plate 305 in FIG. 4. In another example, the lateral plate can be included and the medial plate can be excluded. The design of the augment system 400 without a lateral plate can be used to compensate for a variance on a resected tibia between the medial and lateral sides of the tibia. The first plate 402 can have essentially any thickness and can be thinner or thicker than what is shown in FIG. 5. In another example, separate medial and lateral plates having a generally uniform thickness can be used in substitution for the first plate 402. The medial plate 403 can have essentially any thickness and can be thinner or thicker than what is shown in FIG. 5. In an example, the medial plate 403 can have a generally uniform thickness. In another example, the medial plate 403 can have a variable thickness.

The augment systems 300 and 400 of FIGS. 4 and 5, respectively, include a first plate in combination with at least one of a medial plate and a lateral plate. In other examples, one or more additional plates, like plates 104 and 204, and/or one or more additional medial or lateral plates can be added to the augment system. The augment systems described herein allow for the creation of numerous combinations of augment plates that can be combined based on a patient's particular needs and bone condition.

In addition to defects and abnormalities at a proximal end of the tibia, poor quality bone stock can also exist in the diaphyseal and/or metaphyseal region within the tibia. In those instances, an augment can be used for implantation inside the medullary canal of the tibia. The augment can have a generally cone-shaped outer profile corresponding to a generally cone-shaped bone defect within the tibia. In an example, the cone-shaped augment can be similar to the cone augments disclosed in Publication No. US 2007/0088443 (Ser. No. 11/560,276), filed Nov. 16, 2006 and entitled "PROSTHETIC IMPLANT SUPPORT STRUCTURE" and Publication No. US 2011/0009974 (Ser. No. 12/886,297), filed Sep. 20, 2010 and entitled "TIBIAL AUGMENTS FOR USE WITH KNEE JOINT PROSTHESES, METHOD OF IMPLANTING THE TIBIAL AUGMENT, AND ASSOCIATED TOOLS". The cone-shaped augment can be used in combination with the augment systems 100, 200, 300 and 400 described above. Once implanted inside the medullary canal, a proximal end of the cone-shaped augment can be attached to an inferior surface of a plate of the augment systems described above, using, for example, bone cement, or other types of attachment means, including, for examples, screws.

Figure 6:
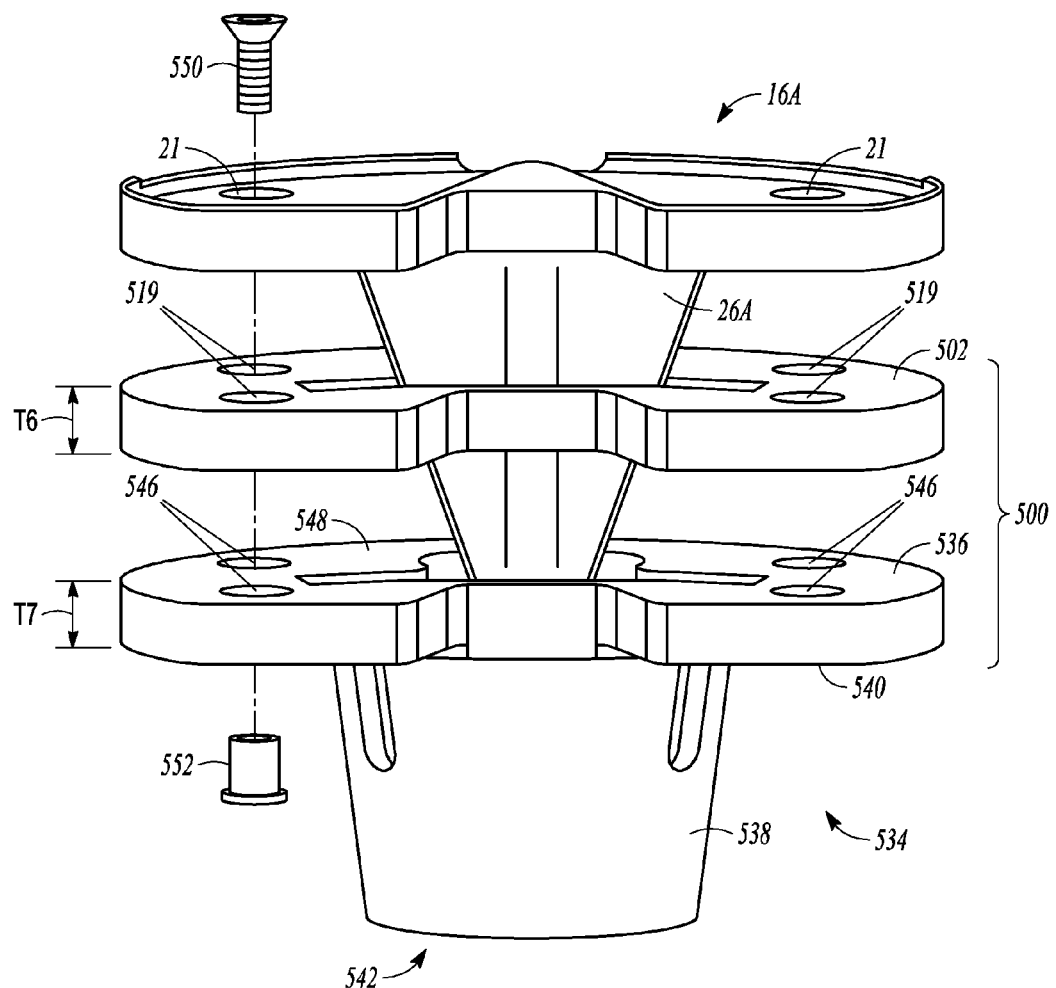
FIG. 6 is a front exploded view of an example of a tibial baseplate and augment system in accordance with the present application.

FIG. 6 shows the tibial baseplate 16A of FIG. 4 and an example of an augment system 500 that can include a support structure 534, which can be used as an alternative to the above-described two-piece combination of a cone-shaped augment and a plate augment. The support structure 534, which is described in further detail below, can include a platform or plate portion 536 and a cone or medullary portion 538. The augment system 500 can also include a first plate 502 that can be in stacked relation to the plate portion 536 of the support structure 534. In an example, the first plate 502 can have a thickness T6 that is generally uniform. In an example, the thickness T6 of the plate 502 can be equal to a thickness T7 of the plate portion 536 of the support structure 534. In other examples, the thickness T6 can be less than or greater than the thickness T7.

It is recognized that in other examples an augment system can include additional augments in a stacked relation with the plate 502 and the support structure 534 shown in FIG. 6. In an example, the augment system 500 can also include one or more additional plates, like the plates described in FIGS. 2 and 3, having a generally uniform thickness or a variable thickness. In an example, the augment system 500 can also include a medial plate and/or a lateral plate as described above in reference to FIGS. 4 and 5. In an example, a medial plate and a lateral plate can be substituted for the first plate 502.

The support structure 534 can be similar to the tibial support structure disclosed in Publication No. US 2012/0310361 (Ser. No. 13/475,721), filed May 18, 2012 and entitled "STABILIZING PROSTHESIS SUPPORT STRUCTURE". In an example, the plate portion 536 and the medullary portion 538 can be monolithically formed as a single piece to create the support structure 534, which can provide a stable implant mounting surface, for use in, for example, a severely damaged or diseased bone. The support structure 534 can provide a foundation for supporting the tibial baseplate 16A, while also facilitating replacement and/or augmentation of metaphyseal or diaphyseal bone within the tibia. As described further below, the tibial baseplate 16A can be mechanically attached to the support structure 534, which can facilitate later removal of the tibial baseplate 16A during a revision surgery while preserving the prosthesis foundation provided by the support structure 534 and ingrown bone.

The medullary portion 538 of the support system 534 can extend distally from an inferior surface 540 of the plate portion 536 and can be generally conically shaped. The medullary portion 538 can include an opening 542 configured to receive the keel 26A and extending from a proximal end of the medullary portion, which is attached to the plate portion 536. In an example, the opening 542 can include a pair of flared cutouts that can accommodate fins present on the keel 26A (see, for example, the fins 28 of the keel 26 in FIG. 1A). In an example, the keel 26A can extend past a distal end of the medullary portion 538 once the augment system 500 is attached to the tibial baseplate 16A. It s recognized that the medullary portion 538 can have varying cross-sectional geometries such as oval, elliptical, or any other non-circular cross-sections. The support system 534 can be configured to accommodate different designs of a tibial baseplate 16A, in addition to the tibial baseplates 16 and 16A shown herein. For example, the support system 534 can be configured for use with a tibial baseplate having one of more pegs, instead of having a keel, or a tibial baseplate having a structurally different keel than the keel 26A.

The plate portion 536 of the support system 534 can include multiple apertures 546 that can extend from a superior surface 548 through the inferior surface 540 of the plate portion 536 and can be used to receive a portion of a fastener, like a fastener 550, for attachment of the support structure 534 and the first plate 502 to the tibial baseplate 16A. As similarly described above for other augment systems, the first plate 502 can include apertures 519. In an example shown in FIG. 6, the fastener 550 can be configured in a top to bottom orientation. In other examples, the fastener 550 can be configured in a bottom to top orientation and can extend up through the plate portion 536 of the support structure 534 to the tibial baseplate 16A.

The fastener 550 is shown in FIG. 6 in combination with a nut 552 for attachment of the plate 502 and the support system 534 to the tibial baseplate 16A. Although only one fastener and one nut are shown in FIG. 6, any number of fasteners/nuts can be used to correspond with a number of apertures in each of the components of the augment system 500. In an example, four fasteners 550 and four nuts 552 can be used in the augment system 500 to correspond to the sets of four apertures 519 and 546 on each of the plate 502 and the plate portion 536, respectively, and to attach the augment system 500 to the tibial baseplate 16A. In an example, the apertures and fasteners 550 can be generally evenly spaced on the tibial baseplate 16A, plate 502 and support system 534 such that a load carried by the fasteners 550 can be generally evenly spread across the surfaces. In other examples, the apertures and fasteners can be randomly spaced on the tibial baseplate 16A, plate 502 and support system 534. The fastener 550 can be available in different lengths to account for various combinations of augment plates and variability in a total thickness of the augment system 500. In addition to the exemplary fastener shown in FIG. 6, any fastener can be used in combination with the augment systems described herein. In an example, the fasteners can include a "collet" type fastener with collet tines that can be spread apart by driving a pin or similar device through a central bore formed in the fastener. The collet fastener can include a single piece attachment mechanism that can include a captured screw to engage the collet. In an example, the fasteners can include a nut and screw design. FIGS. 8A-10 illustrate examples of fasteners usable with the augment systems described herein.

As stated above, in an example, the plate portion 536 and the medullary portion 538 can be monolithically formed as a single piece. In an example, all or a portion of the plate portion 536 and/or the medullary portion 538 can be formed from bone ingrowth material, such as the porous tantalum described above. The porous tantalum can provide a scaffold for the ingrowth and interdigitation of bone with the plate portion 536 and the medullary portion 538. As such ingrowth occurs over time, the support structure 534 can become integrally formed with the tibia to provide a stable, bone-like support foundation for the tibial baseplate 16A. This support foundation can remain in place even if a revision surgery is performed to replace the tibial baseplate 16A with a new tibial baseplate. The plate portion 536 can be secured to the tibial bone without the use of bone cement, although bone cement can still be used if desired.

As similarly described above in reference to FIGS. 2-5, any combination of augment plates can be used with the support structure 534. In other examples, instead of the plate 502, which can be generally sized and shaped to correspond to the tibial baseplate 16A, the augment system 500 can include a medial plate and a lateral plate, which can each have a uniform thickness that is generally equal to one another, or each can have a uniform thickness that is different than the other. In an example, one or both of the medial and lateral plate can have a variable thickness. The augment system 500 can include additional plates in combination with the plate 502 and the support structure 534.

Figure 7A:
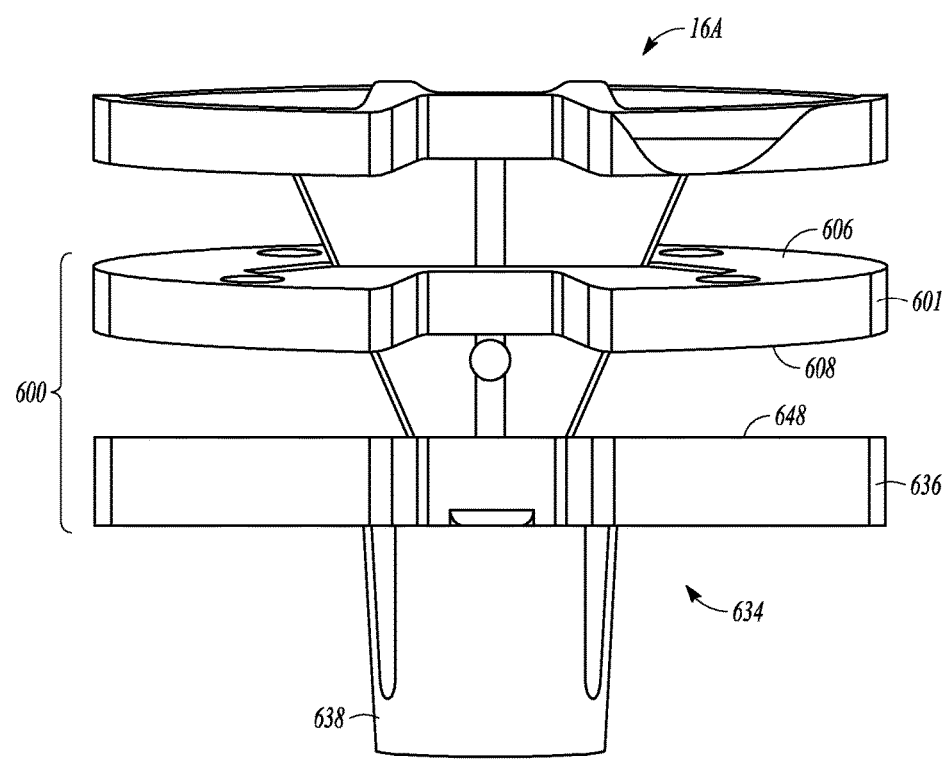
FIG. 7A is a front exploded view of an example of a tibial baseplate and augment system in accordance with the present application.
Figure 7B:
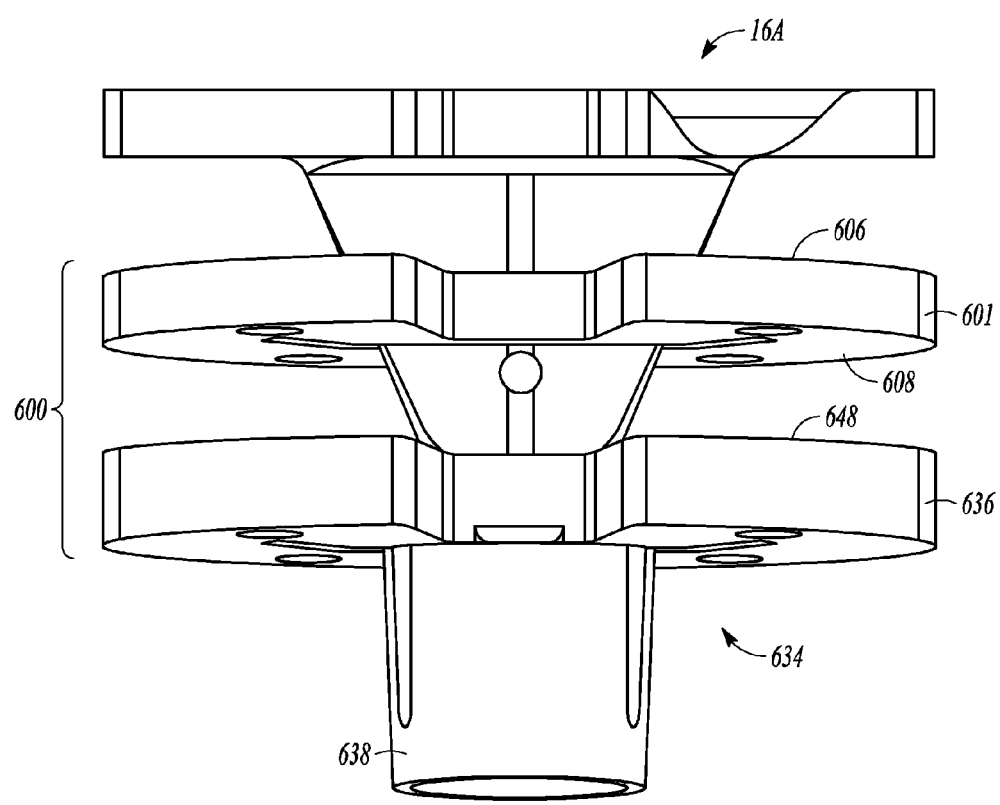
FIG. 7B is alternative front exploded view of the tibial baseplate and augment system of FIG. 7A
Figure 8A:
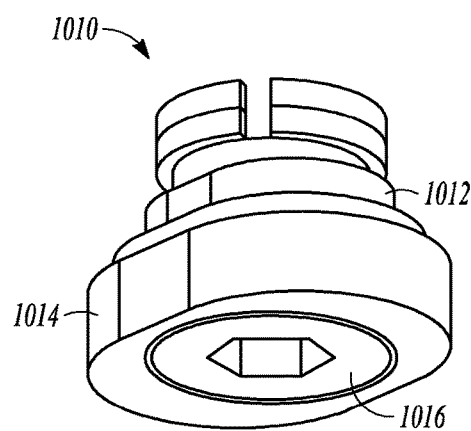
FIG. 8A is a perspective bottom view of an example of a fastener system for use with an augment system.
Figure 8B:
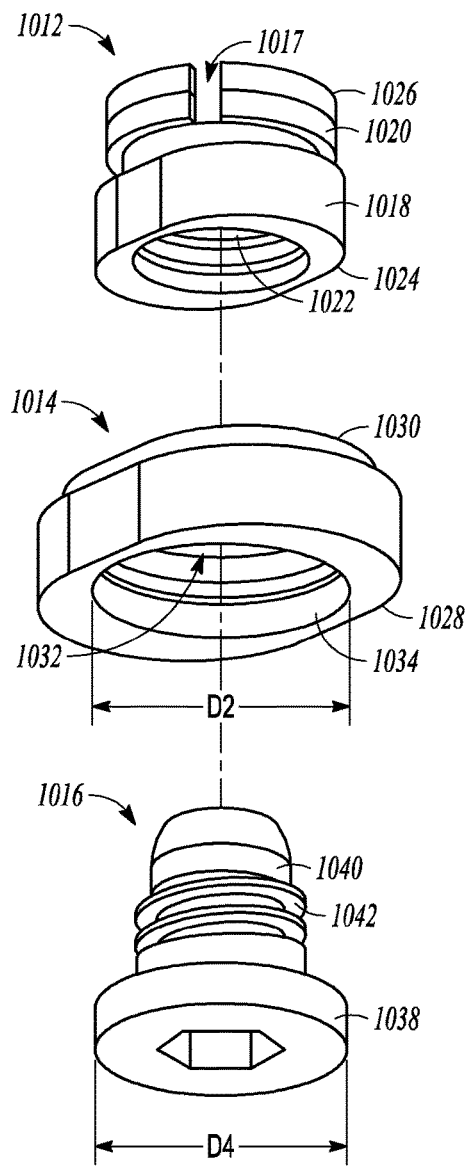
FIG. 8B is an exploded perspective view of the fastener system of FIG. 8A.
Figures 9A, 9B:
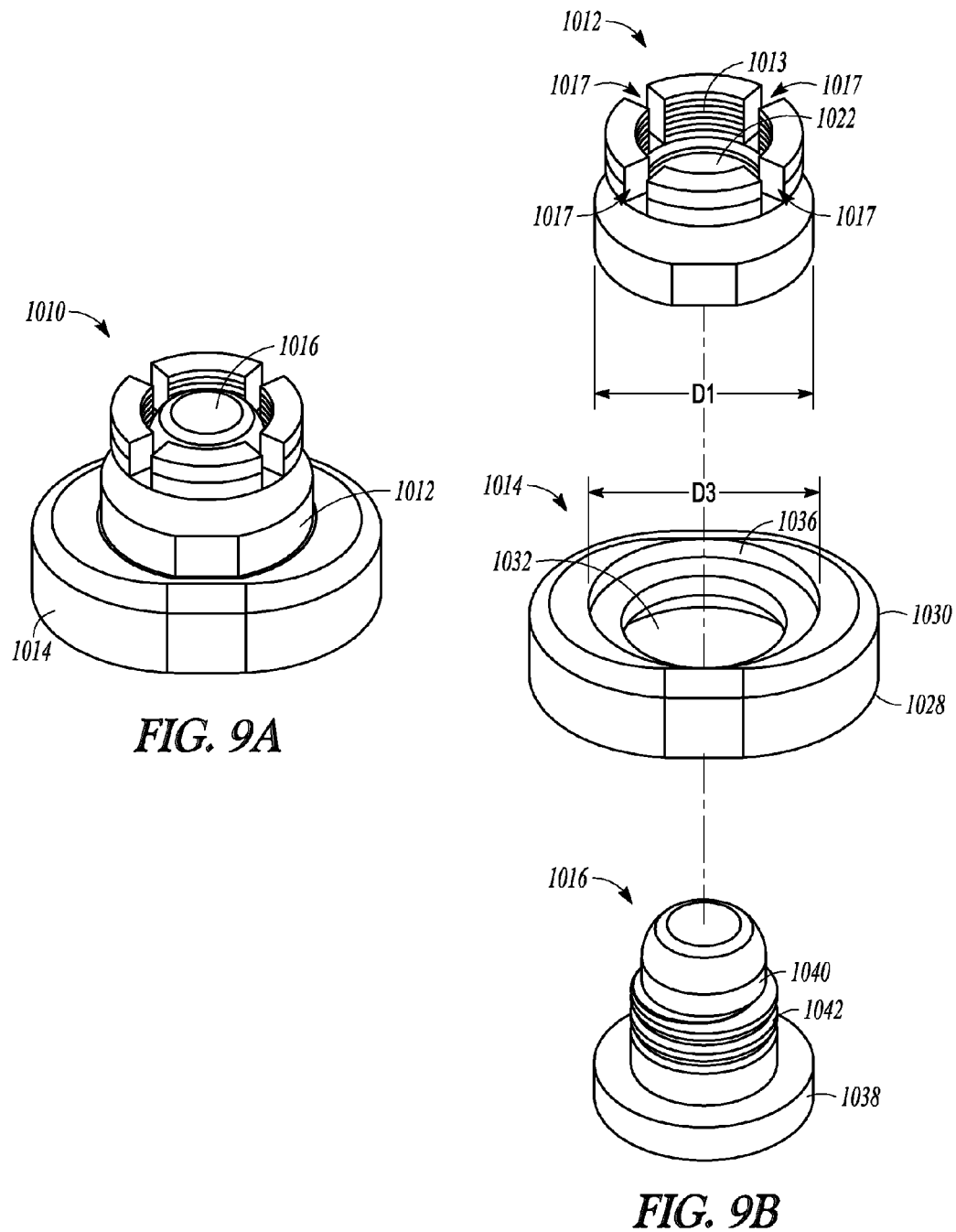
FIG. 9A is a perspective side view of the fastener system of FIGS. 8A-8B.
FIG. 9B is an exploded perspective view of the fastener system of FIG. 9A.

FIGS. 7A and 7B show the tibial baseplate 16A and an example of an augment system 600, which can include, similar to the augment system 500, a plate 601 and a support structure 634. As shown in FIG. 6, the plate 502 of the augment system 500 can have a generally uniform thickness, whereas the plate 601 of FIGS. 7A and 7B can have a variable thickness. In an example, the plate 601 can have an increasing thickness in an anterior-posterior direction such that a thickness of the plate 601 at a posterior end can be less than a thickness of the plate 601 at an anterior end. (FIGS. 7A and 7B show a posterior end of the tibial baseplate 16A.) As such, FIG. 7A shows that a superior surface 606 of the plate 601 can be parallel to the tibial baseplate 16A, and FIG. 7B shows that an inferior surface 608 of the plate 601 can be parallel to a superior surface 648 of the plate portion 636 of the support structure 634. The plate 601 can have a generally uniform thickness in a medial-lateral direction.

An augment system like the augment system 600 can be used when a plate portion 636 of the support structure 634 is not parallel to the tibial baseplate 16A when each is implanted on a resected tibia. In other words, a slope of the plate portion 536 can be different than a slope of a plate portion of the tibial baseplate 16A. In another example, the thickness of the plate 601 at the posterior end can be greater than the thickness of the plate 601 at the anterior end.

The augment systems described herein provide flexibility and versatility to the surgeon or other user by offering numerous combinations of individual augment components that can be used together. Any amount of spacing can be created between a tibial baseplate and the bone, and variation across the resected surface of the bone can be corrected or accommodated. Moreover, defects within the bone can be compensated for by using an augment that extends into the medullary canal in combination with the plate-type augments described herein configured to be located between the tibial baseplate and the resected surface of the tibia.

As stated above, any type of fastener or fastener system can be used with the augment systems described herein to secure the augment plates to one another and to an underside of the tibial baseplate. An example of the fastener 550 and nut 552 was described above in reference to the augment system 500 of FIG. 6.

FIGS. 8A, 8B, 9A and 9B show an example of a fastener system 1010 that can be used with the examples of augment systems described herein and shown in FIGS. 2-7B. The fastener system 1010 can include a nut 1012, a compression body 1014, and a screw 1016. The fastener system 1010 can be configured such that during placement of the fastener system 1010 for attaching two or more parts, the screw 1016, and in some cases, the nut 1012, can 'float' or move relative to the compression body 1014. Reference is made to provisional application, U.S. Ser. No. 61/903,731, entitled "FASTENER SYSTEM", and directed to fastener systems configured to attach two or more parts together, which is incorporated by reference herein in its entirety.

The nut 1012 can include a top portion 1018, a bottom portion 1020, and an opening 1022 formed through the top portion 1018. In an example, the opening 1022 can extend from a top end 1024 to a bottom end 1026 of the nut 1012. In other examples, the opening 1022 can extend from the top end 1024 and into at least a part of the bottom portion 1020 of the nut 1012. The top portion 1018 of the nut 1012 can have an exterior diameter D1. An interior surface 1013 of the nut 1012 can include threads formed in at least a portion of the interior surface 1013.

The bottom portion 1020 of the nut 1012 can include one or more notches or cut-outs 1017 that can be configured to engage with a feature formed on an interior of one of the parts that the fastener system 1010 is intended to hold together, as discussed further below. In an example, the nut 1012 can include four notches 1017 that can be spaced generally equidistant apart. In other examples, the nut 1012 can include more or less notches 1017, or the notches 1017 can be larger or smaller than shown, relative to an overall size of the nut 1012. Other features can be used in addition to or as an alternative to the notches 1017 to engage with the interior of the part.

The compression body 1014 can include a top end 1028, a bottom end 1030, and an opening 1032 formed from the top end 1028 to the bottom end 1030. The compression body 1014 can have a top notch 1034 formed in the opening 1032 at the top end 1028, which is discussed further below. The top notch 1034 can define an interior top diameter D2. In an example, the compression body 1014 can have a bottom notch 1036 formed in the opening 1032 at the bottom end 1030, which can define an interior bottom diameter D3. The top portion 1018 of the nut 1012 can extend into the bottom notch 1036 of the compression body 1014. The exterior diameter D1 of the top portion 1018 of the nut 1012 can be less than the bottom diameter D3 of the compression body 1014. In other examples, the compression body 1014 can exclude the bottom notch 1036, in which case the nut 1012 does not extend into the body 1014, and the top portion 1018 of the nut 1012 can contact, or be near, the compression body 1014 at the bottom end 1030 of the compression body 1014, when the fastener system 1010 is assembled.

The screw 1016 can include a head portion 1038 and an elongated portion 1040. The head portion 1038 can have an exterior head diameter D4 and can be configured to engage with the top notch 1034 in the compression body 1014. The head diameter D4 can be less than the top diameter D2 of the compression body 1014, as discussed further below. At least a portion of the elongated portion 1040 of the screw 1016 can include threads 1042 that can engage with the threads on the interior surface 1013 of the nut 1012. The threads 1042 on the screw 1016 and the threads on the interior surface 1013 of the nut 1012 are examples of locking or securement features for the nut 1012 and screw 1016. It is recognized that other types of features can be used in addition to or as an alternative to the threading on the nut 1012 and the screw 1016, such as, for example, a key and groove combination, or other types of features that generally create a lock once the two components are fully engaged.

The nut 1012, compression body 1014, or screw 1016 can be formed from any material or combination of materials suitable for implantation in a human or animal body. These materials can include plastic, stainless steel, aluminum, titanium, cobalt or one or more alloys thereof.

As described above, the head diameter D4 of the screw 1016 can be less than the top diameter D2 of the compression body 1014. As such, the screw 1016 can move in a radial direction relative to the compression body 1014 during placement of the fastener system 1010 into one or more parts for attaching the one or more parts together. Similarly, in an example in which the compression body 1014 includes the bottom notch 1036, the diameter D1 of the nut 1012 can be less than the bottom diameter D3 of the compression body 1014 such that the nut 1012 can move in a radial direction relative to the compression body 1014 during placement of the fastener system 1010. This design of the fastener system 1010 can make the fastener system 1010 well suited for attaching two or more parts together, including when the two or more parts have multiple apertures configured to receive multiple fasteners.

Figure 10:
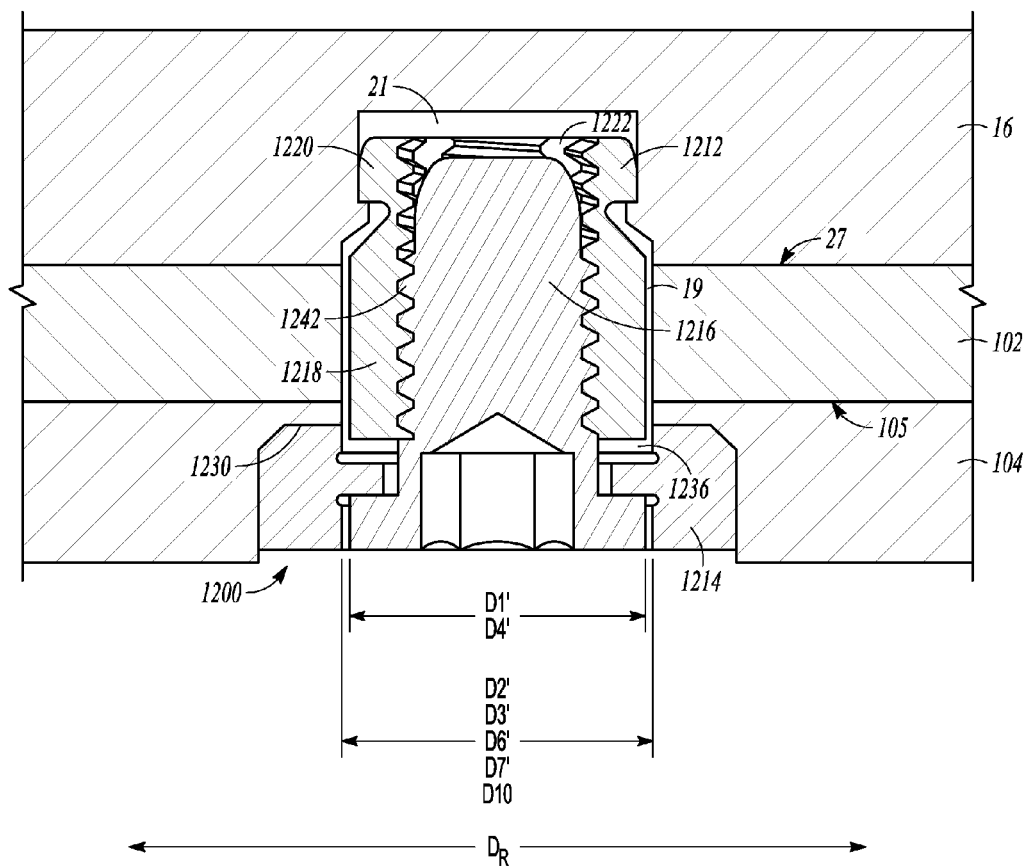
FIG. 10 is a cross-sectional view of a fastener system in use for attaching the augment system of FIG. 2 to a tibial baseplate.

FIG. 10 shows an example of a fastener system 1200 for use in attaching three parts together. The fastener system 1200 can be similar to the fastener system 1010 of FIGS. 8A-9B, and can include a nut 1212, a compression body 1214, and a screw 1216. In an example, the three parts of FIG. 10 can be the second plate 104, first plate 102 and tibial baseplate 16 of FIG. 2. The fastener system 1200 can be used to attach the first 102 and second 104 plates to the inferior surface 50 of the tibial baseplate 16. The tibial baseplate 16 can include one or more apertures 21, and the first 102 and second 104 plates can each include one or more apertures 19 and 23, respectively. In an example, as shown in FIG. 10, the fastener system 1200 can be configured in a bottom to top orientation in which the screw 1216 extends up through the second 104 and first 102 plates, and into the tibial baseplate 16.

The compression body 1214 can be sized and shaped to fit within at least a portion of the aperture 23 of the second plate 104. The nut 1212 can be sized and shaped to be received within at least a portion of the aperture 21 of the tibial baseplate 16 and within at least a portion of the aperture 19 of the first plate 102. The nut 1212 can be received within at least a portion of the aperture 23 of the second plate 104. The screw 1216 can be sized and shaped to be inserted into the compression body 1212 and the nut 1214. The compression body 1214 can be sized and shaped such that the compression body 1214 can have a 'tight fit' with the aperture 23 of the second plate 104—once the compression body 1214 is inserted into the aperture 23, the compression body 1214 can have little to no movement within the aperture 23.

As described above, in reference to the fastener system 1010, a diameter D1' of the top portion 1218 of the nut 1212 can be less than a diameter D3' of the bottom notch 1236 of the compression body 1214. As shown in FIG. 10, this can allow the top portion 1218 of the nut 1212 to move relative to the compression body 1214 in a radial direction (labeled as $D_R$ in FIG. 10). In other examples, the bottom notch 1236 can be excluded from a design of the compression body

1214, in which case the top portion 1218 of the nut 1212 can generally contact, or be in close proximity to, a second end 1230 of the compression body 1214. The diameter D1' of the top portion 1218 of the nut 1212 can be less than a diameter D6' of the aperture 23 of the second plate 104 near a bottom end 105 of the plate 104; alternatively or in addition, the diameter D1' can be less than a diameter D7' of the aperture 21 of the baseplate 16 at or near a bottom end 27 of the tibial baseplate 16, or less than a diameter D10 of the aperture 19 of the first plate 102. As such, the nut 1212 can move in the radial direction $D_R$ relative to the apertures 19, 21 or 23.

As also described above, a diameter D4' of the screw 1216 can be less than a diameter D2' of the top notch 1234 of the compression body 1214. As such, the screw 1216 can move relative to the compression body 1214 in the radial direction $D_R$. In an example, as shown in FIG. 10, the top diameter D1' of the nut 1212 can be generally equal to the top diameter D4' of the screw 1216. Similarly, in an example, as shown in FIG. 10, the diameter D2' of the top notch 1234 can be generally equal to the diameter D3' of the bottom notch 1236. In other examples, the diameter D1' can be less than or greater than the diameter D4', and the diameter D2' can be less than or greater than the diameter D3'.

In an example, the fastener system 1200 can be pre-assembled prior to inserting the fastener system 1200 into the apertures 19 and 23 of the first 102 and second 104 plates, respectively, and the aperture 21 of the tibial baseplate 16. In such an example, the nut 1212 can be aligned with the compression body 1214, and the screw 1216 can be inserted into the nut 1212 and the compression body 1214, prior to inserting the fastener system 1200 into the apertures 19, 21 and 23. Upon insertion of the pre-assembled fastener system 1200 into the apertures 19, 21 and 23, the compression body 1214 can have a generally 'tight fit' within the aperture 23 and can be pressed into place. In contrast, given a diameter difference between the head diameter D4' of the screw 1216 and the top diameter D2' of the compression body 1214, the screw 1216 can initially float after the pre-assembled fastener system 1200 is inserted into the apertures 19, 21 and 23. Similarly, given a diameter difference between the nut diameter D1' and the bottom diameter D3' of the compression body 1214 or between the nut diameter D1' and the diameters D7', D10, and D6' of the apertures 19, 21 and 23, respectively, the nut 1212 can initially float when the pre-assembled fastener system 1200 is placed in the apertures 19, 21 and 23. The nut 1212 or the screw 1216 can each float, or move in the radial direction $D_R$, within the apertures, until each is centered. The screw 1216 can then be tightened, such that the threads 1242 on the screw 1216 can engage with the threads on the interior surface of the nut 1212, thereby causing the screw 1216 and the nut 1212 to be locked into place, along with the compression body 1214.

The nut 1212 can have a longer length as compared to the nut 12 of the fastener system 10. An overall length of the nuts 12 and 1212 can be based on a total thickness of the parts that each of the nuts 12 and 1212 are configured to attach together. In an example, as shown in FIG. 10, a top portion 1218 of the nut 1212 can be longer than the top portion 18 of the nut 12, to increase an overall length of the nut 1212 relative to the nut 12. In an example, a bottom portion 1220 of the nut 1212 can be longer than the bottom portion 20 of the nut 12, to increase an overall length of the nut 1212 relative to the nut 12. In other examples, a length of both the top portion 1218 and the bottom portion 1220 of the nut 1212 can be increased, relative to a length of the top portion 18 and the bottom portion 20, respectively, of the nut 12, to increase an overall length of the nut 1212.

In an example, a plurality of each of the components of the fastener system can be provided to a user as a system, which can be packaged together or separately. The fastener system can be part of an augment system or provided separately. The components of the fastener system can be offered in a variety of sizes in order to be used with different augments intended to be attached together and with different sized or shaped apertures formed in the augments. A plurality of nuts can include nuts having different lengths to accommodate a number and thickness of the augments. The plurality of nuts can also include nuts having different diameters or shapes configured to be used in various size apertures formed in the augments. Similarly, a plurality of screws can include screws having different lengths and diameters to correspond with the plurality of nuts. A plurality of compression bodies can include compression bodies having different diameters or shapes to accommodate the nuts and screws, as well as different size apertures in the augments. Each of the nut, compression and screw components in the system can include the features described above and shown in the figures.

The fastener components can change on demand as specific augment components are tested and selected for a particular patient. In an example, if all the augments and the corresponding tibial baseplate have generally the same size apertures for receiving the fastener system, various screws and nuts can be used as an overall thickness changes based on a thickness of the augment or augments selected. Thus the fastener system offers flexibility to the user. In addition, because the nut and screw are configured to float relative to the compression body, when the fastener system is initially inserted into the apertures of the augments and tibial baseplate, the nut and screw can compensate for potential misalignment of the apertures of each part relative to each other. This can be beneficial when, for example, each of the parts has multiple apertures, configured for multiple fasteners, as shown for the tibial baseplate and augment system of FIG. 6.

As described above, the augment systems of the present application provide flexibility and numerous combinations of stackable augments. In an example, a plurality of augments and a plurality of fasteners can be provided to a user as a system, which can be packaged together or separately. The plurality of augments can include any of the augments described herein (i.e. a full plate, a medial plate, a lateral plate, uniform thickness, variable thickness/wedge, support structure, etc.). The plurality of fasteners can include fasteners having various lengths, and can include any type of fastener, including those described and shown herein, configured for attaching multiple parts together. The plurality of fasteners can include nuts, screws and compression bodies similar to those shown in FIGS. 8A-10. The nuts and screws can be available in various lengths depending on an overall thickness of the augments used for a particular patient.

By having a plurality of augments and fasteners available for use, the surgeon or other user can select a combination of augments and fasteners for use with a tibial baseplate, based on a particular patient's needs and a shape and condition of the patient's tibia. Two or more augments can be attached to an underside of a tibial baseplate and then placed on a proximal end of a resected tibia. In an example, if an orientation of the augments and tibial baseplate on the resected tibia is not satisfactory, one or more augments can be added to the tibial baseplate. In another example, if the orientation of the augments and tibial baseplate is not satisfactory, one or more augments can replace one or more of the original two or more augments. This can be repeated until a satisfactory orientation is achieved. At that point, one or more fasteners can be selected to attach the augments to the tibial baseplate, based on a thickness of the augments and the tibial baseplate at different locations on the tibial baseplate. Fasteners of different lengths can be used for the same tibial baseplate if, for example, the augments include an augment having a variable thickness, or if only one of a medial or lateral augment is used to create additional spacing in one of the medial or lateral compartments.

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls. In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

Method examples described herein can be machine or computer-implemented at least in part. Some examples can include a computer-readable medium or machine-readable medium encoded with instructions operable to configure an electronic device to perform methods as described in the above examples. An implementation of such methods can include code, such as microcode, assembly language code, a higher-level language code, or the like. Such code can include computer readable instructions for performing various methods. The code may form portions of computer program products. Further, in an example, the code can be tangibly stored on one or more volatile, non-transitory, or non-volatile tangible computer-readable media, such as during execution or at other times. Examples of these tangible computer-readable media can include, but are not limited to, hard disks, removable magnetic disks, removable optical disks (e.g., compact disks and digital video disks), magnetic cassettes, memory cards or sticks, random access memories (RAMs), read only memories (ROMs), and the like.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. § 1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

The claimed invention is:

1. An augment system configured for attachment to a tibial baseplate, the augment system comprising:
   a first augment having a superior surface and an inferior surface, the superior surface configured for attachment to an underside of a tibial baseplate; and
   a second augment having a superior surface and an inferior surface, the superior surface configured for attachment to the inferior surface of the first augment or an inferior surface of a third augment configured for placement between the first and second augments,
   wherein the first augment and the second augment are formed of different materials, and
   wherein the second augment includes a porous portion and the inferior surface of the second augment is configured to contact a resected surface of a tibia.

2. The augment system of claim 1 further comprising:
   a third augment having a superior surface and an inferior surface, the superior surface configured for attachment to the inferior surface of the first augment and the inferior surface configured for attachment to the superior surface of the second augment.

3. The augment system of claim 1 wherein the porous portion includes tantalum.

4. The augment system of claim 1 wherein the first augment is configured such that the superior surface attaches to substantially all of the underside of the tibial baseplate, and the second augment is configured such that the superior surface attaches to a portion of the inferior surface of the first augment corresponding to one of a lateral compartment or a medial compartment of the tibial baseplate.

5. The augment system of claim 1 wherein the second augment includes one or both of a medial edge having a different height than a lateral edge in a proximal/distal direction or an anterior edge having a different height than a posterior edge in the proximal/distal direction.

6. The augment system of claim 1 wherein a thickness of the first augment is different than a thickness of the second augment.

7. The augment system of claim 1 further comprising a fastener configured for attaching the first and second augments to the tibial baseplate.

8. The augment system of claim 7 wherein the fastener comprises:
   a nut component having an opening formed through a top portion of the nut component and extending into a bottom portion of the nut component, the nut component configured to be inserted into at least a portion of an aperture in the tibial baseplate and at least a portion of an aperture in the first augment;

a compression component configured to be secured within an aperture in the second augment and including an opening formed from a top end to a bottom end of the compression component and a top notch formed in the top end, the top notch defining a top diameter; and a screw component comprising a head portion having a head diameter and configured to engage with the top notch formed in the compression component, and an elongated portion configured to extend through the opening of the compression component and into the opening of the nut component, wherein the head diameter of the screw component is less than the top diameter of the compression component such that the screw component can move in a radial direction relative to the compression component during insertion of the fastener to attach the first and second augments to the tibial baseplate.

9. A system for use in implanting a tibial prosthesis on a resected tibia, the system comprising:

a plurality of augments, each augment having at least one aperture and configured for attachment to at least one of a tibial baseplate or another augment such that at least two augments are attached to the tibial baseplate in a stacked relation to one another; and a plurality of fasteners having various lengths and configured to attach the at least two augments to the tibial baseplate, wherein the plurality of fasteners includes a plurality of nuts, a plurality of screws, and one or more compression bodies, the plurality of nuts and screws have varying lengths, and a diameter of a head portion of each of the screws is less than a top diameter of each of the compression bodies such that each screw can move in a radial direction relative to the compression body during insertion of a selected nut, screw and compression body in apertures of the plurality of augments and the tibial baseplate.

10. The system of claim 9 wherein a fastener is selected from the plurality of fasteners to attach the at least two augments to the tibial baseplate based on a total thickness of the at least two augments and the tibial baseplate.

11. The system of claim 9 wherein the plurality of augments includes at least one augment having one or both of a medial edge having a different height than a lateral edge in a proximal/distal direction or an anterior edge having a different height than a posterior edge in the proximal/distal direction.

12. The system of claim 9 wherein the plurality of augments includes augments having different thicknesses relative to one another.

13. A method of implanting a tibial prosthesis on a tibia, the method comprising:

attaching at least two augments to an underside of a tibial baseplate to create an augment system, the at least two augments stacked relative to one another, the at least two augments including a first augment formed of a first material and a second augment formed of a second material different than the first material, the second augment including a porous portion;

placing the tibial baseplate and the augment system on a resected surface of the tibia such that an inferior surface of the second augment contacts the resected surface; and when an orientation of the augment system on the resected surface of the tibia is not satisfactory, performing at least one of:

removing one or more of the at least two augments from the augment system, and adding at least one augment to the augment system.

14. The method of claim 13 wherein the performing step is repeated until the orientation of the augment system on the resected surface of the tibia is satisfactory.

15. The method of claim 13 wherein the resected surface of the tibia is angled relative to a transverse plane, and one of the at least two augments is configured to attach to the resected surface.

16. The method of claim 13 wherein the at least two augments includes an augment having one or both of a medial edge having a different height than a lateral edge in a proximal/distal direction or an anterior edge having a different height than a posterior edge in the proximal/distal direction.

17. An augment system configured for attachment to a tibial baseplate, the augment system comprising:

a first augment having a superior surface and an inferior surface, the superior surface configured for attachment to an underside of a tibial baseplate;

a second augment having a superior surface and an inferior surface, the superior surface configured for attachment to the inferior surface of the first augment; and a fastener configured for attaching the first and second augments to the tibial baseplate, the fastener comprising:

a nut component having an opening formed through a top portion of the nut component and extending into a bottom portion of the nut component, the nut component configured to be inserted into at least a portion of an aperture in the tibial baseplate and at least a portion of an aperture in the first augment;

a compression component configured to be secured within an aperture in the second augment and including an opening formed from a top end to a bottom end of the compression component and a top notch formed in the top end, the top notch defining a top diameter; and a screw component comprising a head portion having a head diameter and configured to engage with the top notch formed in the compression component, and an elongated portion configured to extend through the opening of the compression component and into the opening of the nut component, wherein the head diameter of the screw component is less than the top diameter of the compression component such that the screw component can move in a radial direction relative to the compression component during insertion of the fastener to attach the first and second augments to the tibial baseplate.

* * * * *